(12) United States Patent
Libbus et al.

(10) Patent No.: US 7,840,266 B2
(45) Date of Patent: Nov. 23, 2010

(54) INTEGRATED LEAD FOR APPLYING CARDIAC RESYNCHRONIZATION THERAPY AND NEURAL STIMULATION THERAPY

(75) Inventors: Imad Libbus, St. Paul, MN (US); Julio C. Spinelli, Shoreview, MN (US); Randy Westlund, River Falls, WI (US); Julia Moffitt, North Liberty, IA (US); Sophia H. Wang, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 830 days.

(21) Appl. No.: 11/077,970

(22) Filed: Mar. 11, 2005

(65) Prior Publication Data

US 2006/0206153 A1 Sep. 14, 2006

(51) Int. Cl.
*A61N 1/08* (2006.01)
(52) U.S. Cl. .......................... 607/9; 607/122
(58) Field of Classification Search .................. 607/122
See application file for complete search history.

(56) References Cited

U.S. PATENT DOCUMENTS

| | | |
|---|---|---|
| 4,142,530 A | 3/1979 | Wittkampf |
| 4,161,945 A | 7/1979 | Grossman |
| 4,206,398 A | 6/1980 | Janning |
| 4,257,098 A | 3/1981 | Lacy |
| 4,646,754 A | 3/1987 | Seale |
| 4,876,737 A | 10/1989 | Woodworth et al. |
| 4,936,304 A | 6/1990 | Kresh et al. |
| 5,024,222 A | 6/1991 | Thacker |
| 5,199,428 A | 4/1993 | Obel et al. |
| 5,203,326 A | 4/1993 | Collins |
| 5,243,980 A * | 9/1993 | Mehra ........................... 607/6 |
| RE34,663 E | 7/1994 | Seale |

(Continued)

FOREIGN PATENT DOCUMENTS

EP 0581262 A1 2/1994

(Continued)

OTHER PUBLICATIONS

"International Search Report and Written Opinion for Application No. PCT/US2006/008312, dated Jul. 7, 2006", 13 Pages.

(Continued)

*Primary Examiner*—Michael Kahelin
(74) *Attorney, Agent, or Firm*—Faegre & Benson LLP

(57) ABSTRACT

An embodiment includes a main lead assembly having a proximal portion adapted for connection to a device and a distal portion adapted for placement in a coronary sinus, the distal portion terminating in a distal end for placement proximal a left ventricle. Additionally, the main lead assembly includes a left ventricular electrode located at its distal end which is adapted to deliver cardiac resynchronization therapy to reduce ventricular wall stress. The main lead assembly also includes a fat pad electrode disposed along the main lead assembly a distance from the distal end to position the fat pad electrode proximal to at least one parasympathetic ganglia located in a fat pad bounded by an inferior vena cava and a left atrium. The fat pad electrode is adapted to stimulate the parasympathetic ganglia to reduce ventricular wall stress.

23 Claims, 13 Drawing Sheets

U.S. PATENT DOCUMENTS

| | | | |
|---|---|---|---|
| 5,356,425 A | 10/1994 | Bardy et al. | |
| 5,411,531 A | 5/1995 | Hill et al. | |
| 5,477,858 A | 12/1995 | Norris et al. | |
| 5,507,784 A * | 4/1996 | Hill et al. | 607/14 |
| 5,514,174 A | 5/1996 | Heil, Jr. et al. | |
| 5,578,061 A | 11/1996 | Stroetmann et al. | |
| 5,645,570 A | 7/1997 | Corbucci | |
| 5,720,768 A | 2/1998 | Verboven-Nelissen | |
| 5,796,703 A | 8/1998 | Schell et al. | |
| 5,803,928 A | 9/1998 | Tockman et al. | |
| 5,875,158 A | 2/1999 | Schell | |
| 5,902,324 A | 5/1999 | Thompson et al. | |
| 6,006,134 A | 12/1999 | Hill et al. | |
| 6,119,043 A | 9/2000 | Hsu et al. | |
| 6,134,470 A * | 10/2000 | Hartlaub | 607/14 |
| 6,341,236 B1 | 1/2002 | Osorio et al. | |
| 6,522,926 B1 | 2/2003 | Kieval et al. | |
| 6,544,270 B1 | 4/2003 | Zhang | |
| 6,584,362 B1 * | 6/2003 | Scheiner et al. | 607/122 |
| 6,611,713 B2 | 8/2003 | Schauerte | |
| 6,741,529 B1 | 5/2004 | Getreuer | |
| 6,839,592 B2 | 1/2005 | Grandjean | |
| 6,900,708 B2 | 5/2005 | White et al. | |
| 6,922,589 B2 | 7/2005 | Stahmann et al. | |
| 6,937,896 B1 | 8/2005 | Kroll | |
| 6,942,622 B1 | 9/2005 | Turcott | |
| 6,988,007 B1 * | 1/2006 | Morgan et al. | 607/123 |
| 7,031,474 B1 | 4/2006 | Yuen et al. | |
| 7,058,449 B2 | 6/2006 | Stahmann et al. | |
| 7,069,070 B2 | 6/2006 | Carlson et al. | |
| 7,092,755 B2 | 8/2006 | Florio | |
| 7,123,961 B1 | 10/2006 | Kroll et al. | |
| 7,139,607 B1 | 11/2006 | Shelchuk | |
| 7,139,614 B2 | 11/2006 | Scheiner et al. | |
| 7,191,015 B2 * | 3/2007 | Lamson et al. | 607/119 |
| 7,245,967 B1 | 7/2007 | Shelchuk | |
| 7,277,761 B2 | 10/2007 | Shelchuk | |
| 7,333,854 B1 | 2/2008 | Brewer et al. | |
| 7,403,819 B1 | 7/2008 | Shelchuk et al. | |
| 7,480,532 B2 | 1/2009 | Kieval et al. | |
| 7,570,999 B2 | 8/2009 | Libbus et al. | |
| 7,587,238 B2 | 9/2009 | Moffitt et al. | |
| 2001/0020136 A1 | 9/2001 | Sweeney et al. | |
| 2002/0035378 A1 | 3/2002 | Bardy et al. | |
| 2002/0058877 A1 | 5/2002 | Baumann et al. | |
| 2002/0077670 A1 | 6/2002 | Archer et al. | |
| 2002/0091415 A1 | 7/2002 | Lovett et al. | |
| 2002/0116030 A1 | 8/2002 | Rezai | |
| 2003/0004549 A1 | 1/2003 | Hill et al. | |
| 2003/0040774 A1 | 2/2003 | Terry et al. | |
| 2003/0045909 A1 | 3/2003 | Gross et al. | |
| 2003/0078623 A1 | 4/2003 | Weinberg et al. | |
| 2003/0100924 A1 | 5/2003 | Foreman et al. | |
| 2003/0199958 A1 | 10/2003 | Zhang et al. | |
| 2003/0236575 A1 | 12/2003 | Yu et al. | |
| 2004/0015193 A1 | 1/2004 | Lamson et al. | |
| 2004/0054381 A1 | 3/2004 | Pastore et al. | |
| 2004/0088015 A1 | 5/2004 | Casavant et al. | |
| 2004/0098057 A1 | 5/2004 | Pastore et al. | |
| 2004/0116970 A1 | 6/2004 | Girouard et al. | |
| 2004/0138721 A1 | 7/2004 | Osorio et al. | |
| 2004/0172075 A1 * | 9/2004 | Shafer et al. | 607/9 |
| 2004/0193231 A1 | 9/2004 | David et al. | |
| 2004/0199210 A1 | 10/2004 | Shelchuk | |
| 2004/0215274 A1 | 10/2004 | Kerver et al. | |
| 2005/0059897 A1 | 3/2005 | Snell et al. | |
| 2005/0065555 A1 | 3/2005 | Er | |
| 2005/0096705 A1 | 5/2005 | Pastore et al. | |
| 2005/0143785 A1 | 6/2005 | Libbus | |
| 2005/0149126 A1 | 7/2005 | Libbus | |
| 2005/0149127 A1 | 7/2005 | Libbus | |
| 2005/0149128 A1 | 7/2005 | Heil et al. | |
| 2005/0149129 A1 | 7/2005 | Libbus et al. | |
| 2005/0149130 A1 | 7/2005 | Libbus | |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus et al. | |
| 2005/0149155 A1 | 7/2005 | Scheiner et al. | |
| 2005/0149156 A1 | 7/2005 | Libbus et al. | |
| 2005/0222632 A1 | 10/2005 | Obino | |
| 2005/0248418 A1 | 11/2005 | Govind et al. | |
| 2005/0251216 A1 | 11/2005 | Hill et al. | |
| 2006/0079945 A1 | 4/2006 | Libbus | |
| 2006/0095080 A1 | 5/2006 | Libbus et al. | |
| 2006/0106429 A1 | 5/2006 | Libbus et al. | |
| 2006/0134071 A1 | 6/2006 | Ross et al. | |
| 2006/0134079 A1 | 6/2006 | Sih et al. | |
| 2006/0136027 A1 | 6/2006 | Westlund et al. | |
| 2006/0136028 A1 | 6/2006 | Ross et al. | |
| 2006/0206154 A1 | 9/2006 | Moffitt et al. | |
| 2006/0206159 A1 | 9/2006 | Moffitt et al. | |
| 2006/0224188 A1 | 10/2006 | Libbus et al. | |
| 2006/0253156 A1 | 11/2006 | Pastore et al. | |
| 2006/0271115 A1 | 11/2006 | Ben-Ezra et al. | |
| 2007/0067008 A1 | 3/2007 | Scheiner et al. | |
| 2007/0123923 A1 | 5/2007 | Lindstrom et al. | |
| 2007/0142871 A1 | 6/2007 | Libbus et al. | |
| 2008/0125843 A1 | 5/2008 | Ben-David et al. | |
| 2008/0172104 A1 | 7/2008 | Kieval et al. | |

FOREIGN PATENT DOCUMENTS

| | | |
|---|---|---|
| EP | 1304135 A2 | 4/2003 |
| EP | 1421973 A2 | 5/2004 |
| WO | WO-9965561 A1 | 12/1999 |
| WO | WO-02087694 A1 | 11/2002 |
| WO | WO-03020364 A2 | 3/2003 |
| WO | WO-2005113066 A1 | 12/2005 |
| WO | WO-2006098996 A1 | 9/2006 |
| WO | WO-2007078410 A1 | 7/2007 |

OTHER PUBLICATIONS

Abraham, W. T., "MIRACLE Study Group. Multicenter InSync Randomized Clinical Evaluation. Cardiac resynchronization in chronic heart failure", *New England Journal of Medicine*, 346(24 ), (Jul. 13, 2002), 1845-53.

Bocker, D., "Ventricular Resynchronization Therapy May Restore Autonomic Balance as Evidenced by Redicung the Low Frequency to High Frequency Autonomic Ratio in Heart Failure Patients", *4th International Meeting organized by the Working Group on Heart Failure of the European Society of Cardiology (Abstract)*, Barcelona, Spain,(Jun. 11, 2001), 1 p.

Dickerson, L. W., "Parasympathetic neurons in the cranial medial ventricular fat pad on the dog heart selectively decrease ventricular contractility", *Journal of the Autonomic Nervous System*, 70(1-2), (May 28, 1998), 129-41.

Gatti, P. J., "Vagal control of left ventricular contractility is selectively mediated by a cranioventricular intracardiac ganglion in the cat", *Journal of the Autonomic Nervous System*, vol. 66, No. 3, (Oct. 13, 1997), 138-144.

Henning, R. J., "Vagal stimulation attenuates sympathetic enhancement of left ventricular function", *American Journal of Physiology*, 258(5 Pt 2), (May 1990), H1470-5.

Ishise, H., "Time course of sympathovagal imbalance and left ventricular dysfunction in conscious dogs with heart failure", *Journal of Applied Physiology*, 84(4), (Apr. 1998), 1234-41.

Libbus, Imad, "Implantable Device for Treating Epilepsy and Cardiac Rhythm Disorders", U.S. Appl. No. 11/312,178, filed Dec. 21, 2005, 39 Pages.

Schauerte, P., "Catheter stimulation of cardiac parasympathetic nerves in humans: a novel approach to the cardiac autonomic nervous system", *Circulation*, 104(20), (Nov. 13, 2001), 2430-5.

Schauerte, Patrick, et al., "Focal Atrial Fibrillation: Experimental Evidence for a", *Journal of Cardiovascular Electrophysiology*, vol. 12, No. 5, (May 2001), 592-599.

Schauerte, Patrick N., et al., "Transvenous parasympathetic cardiac nerve stimulation: an approach for stable sinus rate control", *Journal of Cardiovascular Electrophysiology*, 10(11), (Nov. 1999), 1517-24.

Schauerte, Patrick N., "Transvenous Parasympathetic Nerve Stimulation in the Inferior Vena Cava and Atrioventricular Conduction", *Journal of Cardiovascular Electrophysiology*, 11(1), (Jan. 2000), 64-69.

Scheiner, Avram, et al., "Leads For Pacing and/or Sensing The Heart From Within The Coronary Veins", U.S. Appl. No. 11/600,807, filed Nov. 16, 2006, 43 pages.

Takahashi, N., "Vagal modulation of ventricular tachyarrhythmias induced by left ansae subclaviae stimulation in rabbits", *Japanese Heart Journal*, 39(4), (Jul. 1998), 503-11.

Wallick, D. W., "Selective AV nodal vagal stimulation improves hemodynamics during acute atrial fibrillation in dogs", *American Journal of Physiology—Heart & Circulatory Physiology*, 281(4), (Oct. 2001), H1490-7.

Zhang, Y., "Optimal ventricular rate slowing during atrial fibrillation by feedback AV nodal-selective vagal stimulation", *American Journal of Physiology—Heart & Circulatory Physiology*, 282(3), (Mar. 2002), H1102-10.

Zhou, X., "Prevention of high incidence of neurally mediated ventricular arrhythmias by afferent nerve stimulation in dogs", *Circulation*, 101(7), (Feb. 22, 2000), 819-24.

"U.S. Appl. No. 11/078,460, Response filed Apr. 18, 2008 to Non-Final Office Action mailed Jan. 18, 2008", 14 pages.

"U.S. Appl. No. 11/078,460, Non-Final Office Action mailed Jan. 18, 2008", 7 pgs.

"U.S. Appl. No. 10/700,368, Non-Final Office Action mailed Feb. 25, 2009", 13 pgs.

"U.S. Appl. No. 10/700,368, Response filed Jan. 15, 2009 to Final Office Action mailed Oct. 15, 2008", 8 pgs.

"U.S. Appl. No. 10/700,368, Response filed Jun. 16, 2008 to Non-Final Office Action mailed Mar. 14, 2008", 8 pgs.

"U.S. Appl. No. 10/700,368, Final Office Action mailed Oct. 15, 2008", 12 pgs.

"U.S. Appl. No. 11/078,460, Response filed Sep. 29, 2008 to Final Office Action mailed Jul. 30, 2008", 11 pgs.

"U.S. Appl. No. 11/078,460, Notice of Allowance Mailed on Nov. 10, 2008", 7 Pgs.

"U.S. Appl. No. 11/078,460, Final Office Action mailed Jul. 30, 2008", 7 pgs.

Chiou, C. W, et al., "Efferent vagal innervation of the canine atria and sinus and atrioventricular nodes. The third fat pad.", *Circulation*, 95(11), (Jun. 3, 1997), 2573-84.

"U.S. Appl. No. 10/700,368, Notice of Allowance mailed Sep. 15, 2009", 8 pgs.

"U.S. Appl. No. 10/700,368, Response filed Jul. 20, 2009 to Non Final Office Action mailed Feb. 25, 2009", 11 pgs.

"U.S. Appl. No. 10/982,001, Examiner Interview Summary filed Oct. 3, 2008", 2 pgs.

"U.S. Appl. No. 10/982,001, Examiner Interview Summary mailed Sep. 15, 2008", 4 pgs.

"U.S. Appl. No. 10/982,001, Final Office Action mailed Jun. 4, 2009", 15 pgs.

"U.S. Appl. No. 11/078,460, Notice of Allowance mailed May 1, 2009", 4 pgs.

"U.S. Appl. No. 11/312,178, Notice of Allowance mailed Apr. 3, 2009", 6 pgs.

"European Application Serial No. 06827323.4, Communication mailed Jun. 2, 2009", 2 pgs.

"European Application Serial No. 06827323.4, Response filed Apr. 24, 2009 to Communication mailed Nov. 12, 2008", 6 pgs.

Search Report issued in EP 06737480, mailed Mar. 10, 2010, 7 pages.

Murakawa, Y. et al., "Effect of Cervical Vagal Nerve Stimulation on Defibrillation Energy", Japanese Heart Journal, Japanese Heart Journal Association, JP vol. 44, No. 1, Jan. 1, 2003, pp. 91-100, XP002462211, ISSN: 0021-4868.

Zhang, Y. et al., "Achieving regular slow rhythm during atrial fibrillation without atrioventricular nodal ablation: Selective vagal stimulation plus ventricular pacing", Heart Rhythm, Elsevier vol. 1, No. 4, Oct. 1, 2004, pp. 469-475, XP004608379 ISSN: 1547-5271.

* cited by examiner

INTEGRATED LEAD FOR APPLYING CARDIAC RESYNCHRONIZATION THERAPY AND NEURAL STIMULATION THERAPY

CROSS REFERENCE TO RELATED APPLICATIONS

The following commonly assigned U.S. patent is related and incorporated herein by reference in its entirety: "Leads for Pacing and/or Sensing the Heart from Within the Coronary Veins," U.S. Pat. No. 6,584,362, filed Aug. 30, 2000, issued Jun. 24, 2003. The following commonly assigned U.S. patent applications are related and are all herein incorporated by reference in their entirety: "Multi-site Ventricular Pacing Therapy with Parasympathetic Stimulation," Ser. No. 10/700,368, filed Nov. 3, 2003; "Combined Transvascular Neural Stimulation and Cardiac Resynchronization Therapy," Ser. No. 11/078,460, filed Mar. 11, 2005; "System and Method for Filtering Neural Stimulation," Ser. No. 10/982,001, filed Nov. 4, 2004.

TECHNICAL FIELD

This application relates generally to implantable medical devices and, more particularly, to methods and apparatus for providing cardiac resynchronization therapy and neural stimulation therapy.

BACKGROUND

Various pathologies of the heart decrease efficiency of the cardiac system. For example, reduced autonomic balance (an increase in sympathetic and a decrease in parasympathetic cardiac tone) has been shown to be associated with cardiac dysfunction, and in particular, left ventricular dysfunction. Additional pathologies which affect the manner and degree to which the heart chambers contract during a cardiac cycle also effect cardiac efficiency. For example, the heart pumps more effectively when the chambers contract in a coordinated manner, a result normally provided by specialized conduction pathways. Nominal function of these pathways synchronize contractions, promoting hemodynamic efficiency. Without synchronization, the heart's pumping efficiency is diminished.

During abnormal cardiac function, including during and after myocardial infarction, myocytes die and are replaced by scar tissue, which has different mechanical and elastic properties than functional myocardium. Over time, these tissues can become thin and expand, causing a redistribution of myocardial stresses over the heart, a phenomenon called remodeling. Eventually, this process leads to impaired mechanical function and heart failure.

SUMMARY

According to various embodiments the present subject matter increases parasympathetic tone and reduces sympathetic tone to diminish the effects of remodeling, and electrically stimulates selected heart chambers to improve hemodynamic efficiency and reduce stress contributing to remodeling. Additionally, sympathetic inhibition can reduce arrhythmia.

In various embodiments, the present subject matter includes a main lead assembly having a proximal portion adapted for connection to a device and a distal portion adapted for placement in a coronary sinus, the distal portion terminating in a distal end for placement proximal a left ventricle. Additionally, the main lead assembly includes a left ventricular electrode located at its distal end which is adapted to deliver cardiac resynchronization therapy to reduce ventricular wall stress. The main lead assembly also includes a fat pad electrode disposed along the main lead assembly a distance from the distal end to position the fat pad electrode proximal a parasympathetic ganglia located in a fat pad bounded by an inferior vena cava and a left atrium. The fat pad electrode is adapted to stimulate the parasympathetic ganglia to reduce ventricular wall stress.

Various embodiments of the present subject matter include a main lead assembly sized for placement in a coronary sinus and proximal a left ventricle. The main lead assembly has a proximal portion and a distal portion and defines a puncture body lumen extending along the main lead assembly. Also, the main lead assembly includes a steerable extravascular lead body slidably disposed in the puncture body lumen. The steerable extravascular lead body has a near portion positioned at the proximal portion of the main lead assembly and a far portion extending to a distance along the puncture body lumen to locate the far portion proximal a fat pad bounded by an inferior vena cava and a left atrium. The steerable extravascular lead body is adapted to puncture the main lead assembly. A fat pad electrode is connected to the steerable extravascular lead body at the far portion. The fat pad electrode is adapted to stimulate parasympathetic ganglia located in the fat pad bounded by the inferior vena cava and the left atrium to reduce ventricular wall stress.

In various embodiments, the present subject matter includes a method where a left ventricular electrode is placed proximal a left ventricle, a fat pad electrode is placed proximal at least one parasympathetic ganglion located in a fat pad bounded by an inferior vena cava and a left atrium, and a right ventricular electrode is placed proximal a right ventricle. Ventricular wall stress is reduced by delivering cardiac resynchronization therapy to the left ventricular electrode and the right ventricular electrode and delivering electrical pulses to the fat pad electrode to induce parasympathetic response.

In various embodiments, the present subject matter includes means for positioning a left ventricle electrode proximal a left ventricle. The left ventricular electrode is adapted to be used to deliver cardiac resynchronization therapy to reduce ventricular wall stress. Also included are means for positioning a fat pad electrode proximal parasympathetic ganglia located in a fat pad bounded by a inferior vena cava and a left atrium. The fat pad electrode is adapted to stimulate the parasympathetic ganglia located in the fat pad bounded by the inferior vena cava and the left atrium to reduce ventricular wall stress.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

In the drawings, matching numbers refer to similar components. For example, if two figures have features which have matching numbers, those features are similar.

DETAILED DESCRIPTION

Figure 1:
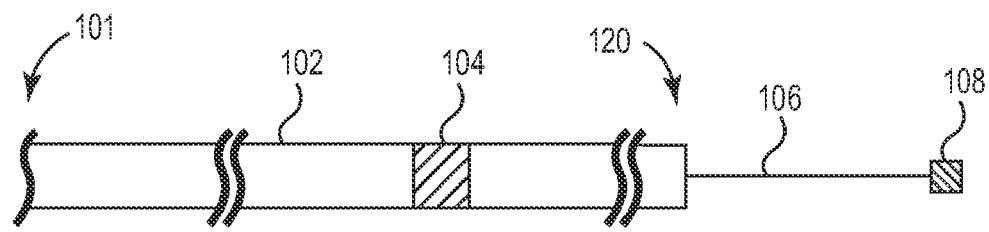
FIG. 1 shows a lead adapted to deliver neural stimulation and ventricular stimulation, according to various embodiments of the present subject matter.

The following detailed description of the present subject matter refers to the accompanying drawings which show, by way of illustration, specific aspects and embodiments in which the present subject matter can be practiced. These embodiments are described in sufficient detail to enable those skilled in the art to practice the present subject matter. Other embodiments can be utilized and structural, logical, and electrical changes can be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter relates to devices and methods to reduce ventricular wall stress and provides a therapy that combining cardiac resynchronization therapy and neural stimulation to induce parasympathetic response. Various aspects of the present subject matter include application of the combined therapy enabled by a single, integrated lead for placement in the left side of the heart capable of stimulating nerve fibers to induce parasympathetic response. The lead is capable of being used to provide cardiac resynchronization therapy, such as when combined with a lead adapted for placement in the right side of the heart for stimulation of the right ventricle. Alternative embodiments position the lead elsewhere.

The degree to which a heart muscle fiber is stretched before it contracts is termed preload. The maximum tension and velocity of shortening of a muscle fiber increases with increasing preload. When a myocardial region contracts late relative to other regions, the contraction of those opposing regions stretches the later contracting region and increases the preload.

The degree of tension or stress on a heart muscle fiber as it contracts is termed afterload. Because pressure within the ventricles rises rapidly from a diastolic to a systolic value as blood is pumped out into the aorta and pulmonary arteries, the parts of the ventricle that first contract due to an excitatory stimulation do so against a lower afterload than do parts of the ventricle contracting later.

Overall, a myocardial region which contracts later than other regions is subjected to both an increased preload and afterload, causing uneven stress to the ventricular wall. The heart's initial physiological response to the uneven stress resulting from an increased preload and afterload is compensatory hypertrophy in those later contracting regions of the myocardium. In the later stages of remodeling, the regions can undergo atrophic changes with wall thinning due to the increased stress, and the extent of remodeling is positively correlated with mortality in heart failure patients.

One mode of remodeling is created by the ventricular conduction delays associated with heart failure and ventricular dysfunction. The condition can arise from autonomic imbalance. The automatic (or autonomic) nervous system regulates "involuntary" organs, while the contraction of voluntary (skeletal) muscles is controlled by somatic motor nerves. Examples of involuntary organs include respiratory and digestive organs, blood vessels and the heart. Often, the automatic nervous system functions in an involuntary, reflexive manner to regulate organs such as glands, muscles in the skin, the eye, the stomach, intestines and the bladder. These descriptions are not exhaustive or exclusive, but are provided for illustration.

The automatic nervous system includes, but is not limited to, the sympathetic nervous system and the parasympathetic nervous system. The sympathetic nervous system is affiliated with stress and the "fight or flight response" to patient stimulus. Among other effects, the "fight or flight response" increases blood pressure and heart rate to increase skeletal muscle blood flow, and decreases digestion to provide energy for "fighting or fleeing." The parasympathetic nervous system is affiliated with relaxation and the "rest and digest response" which, among other effects, decreases blood pressure and heart rate, and increases digestion to conserve energy. The automatic nervous system maintains normal internal function and works with the somatic nervous system.

Sympathetic and parasympathetic nerves act on the heart via beta-adrenergic and muscarinic receptors, respectively, to affect both heart rate and myocardial contractility. A predominance of sympathetic over parasympathetic stimulation of the heart, for example, increases both intrinsic heart rate (via receptors at the sino-atrial node) and the strength of ventricular contractions. Stimulation of cardiac parasympathetic nerves, on the other hand, decreases myocardial contractility and hence reduces ventricular wall stresses. Sympathetic inhibition, as well as parasympathetic activation, has also been associated with reduced arrhythmia vulnerability following a myocardial infarction, presumably by increasing collateral perfusion of the acutely ischemic myocardium and decreasing myocardial damage.

In addition to effects influencing heart rate, the automatic nervous system also impacts the health of cardiac myocytes. Increased sympathetic nervous system activity following ischemia often results in increased exposure of the myocardium to epinephrine and norepinephrine. These catecholamine examples activate intracellular pathways within the myocytes, which lead to myocardial death and fibrosis. Stimulation of the parasympathetic nerves, including the vagus nerve, inhibits this effect.

Ventricular dysynchrony and autonomic imbalance contribute to cardiac remodeling. Therapies directed at these areas are useful. For example, improving ventricular synchrony is one way to treat cardiac remodeling.

Myocardium which contracts earlier in the cycle is subjected to less stress and is less likely to undergo hypertrophic remodeling. This phenomenon is used to cause reversal of remodeling by pacing one or more sites in a heart chamber with one or more excitatory stimulation pulses during a cardiac cycle with a specified pulse output sequence. The stimulation is delivered in a manner that excites a previously stressed and remodeled region of the myocardium earlier during systole so that it experiences less afterload and preload. The pre-excitation of the remodeled region relative to other regions unloads the region from mechanical stress and allows reversal of remodeling to occur.

Multi-site pacing, in various embodiments, is applied to one chamber, but in many embodiments includes two heart chambers. For example, a chamber is paced at multiple sites with excitatory stimulation pulses in order to produce multiple waves of depolarization emanating from the pacing sites. This can produce a more coordinated contraction of the ventricle and thereby compensate for intraventricular conduction defects. Biventricular pacing is an example of a resynchronization therapy in which both ventricles are paced together. Some biventricular applications pace the ventricles with a simultaneous pulse, and others include a short delay between a right pulse and a left pulse.

Thus, patients can benefit from multi-site ventricular pacing for the purpose of improving cardiac output with more coordinated contractions and for the purpose of reducing ventricular wall stresses. Multi-site pacing also compensates effects of parasympathetic response stimulation such as reduction in cardiac output. For example, a patient's metabolism can demand higher output than is available under a parasympathetic response pacing mode, and multi-site pacing can adjust to this demand.

What follows is a description of an implantable cardiac device used to practice various forms of therapy. An implantable cardiac device is typically placed subcutaneously or submuscularly in a patient's chest with leads running intravenously into the heart to connect the device to electrodes used for sensing and stimulation. Leads can also be positioned on the epicardium by various means. A programmable electronic controller causes the stimulus pulses to be output in response to lapsed time intervals and sensed electrical activity (i.e., intrinsic heart beats not as a result of a stimulus pulse). The device senses intrinsic cardiac electrical activity by means of electrodes disposed near the chamber to be sensed. A depolarization wave associated with an intrinsic contraction of the atria or ventricles that is detected by the device is referred to as an atrial sense or ventricular sense, respectively. In order to cause such a contraction in the absence of an intrinsic beat, a stimulus pulse (also referred to as a pace or pacing pulse when delivered in order to enforce a certain rhythm) with energy above a certain threshold is delivered to the chamber.

In various embodiments, an electrical stimulus originates from a central device and travels over conductive channels to arrive at an intended location. For example, multiple embodiments include a cardiac rhythm device and one or more leads running from the device to the heart. In one embodiment, the device includes a housing used to sense patient information, and in some cases the housing is used to deliver electrical stimulation. Additionally, various embodiments use electrodes present on the one or more leads to sense and deliver electrical signals.

Thus, in various embodiments, the device uses information gathered from sensors to deduce cardiac function. Various embodiments include a combination of cardiac resynchronization therapy and neural stimulation applied in a closed-loop manner in response to physiological parameters, such as heart rate changes induced by stimulation from the device, or intrinsic heart rate changes.

For example, selective stimulation of autonomic epicardial ganglia within cardiac fat pads, the fat pad located proximal the inferior vena cava-left atrial junction ("IVC-LA"), activates the parasympathetic nervous system to produce some of the benefits mentioned here. In various embodiments, this stimulation is delivered by an implantable cardiac device via an electrode incorporated into a lead. In various embodiments, the electrode is incorporated within a lead used for cardiac rhythm management therapy to the heart. A pulse generator delivers electrical stimulation via an electrode and stimulates the parasympathetic nerves that extend proximal to the electrode. Electrical stimulation of the parasympathetic nervous system can be, for example, in the form of a square-wave or truncated exponential pulse train at a frequency of between 5 and 50 Hz. The result of such electrical stimulation is a slowing of sinus rhythm due to increased parasympathetic activity acting on the sino-atrial node as well as a negative inotropic effect which decreases ventricular wall stresses during systole.

Examples of these systems include devices programmed to modulate the delivery of parasympathetic stimulation in accordance with a sensed parameter which reflects the patient's demand for cardiac output and the patient's actual cardiac output. In some embodiments, the device measures the patient's exertion level with one or both of a minute ventilation sensor and an accelerometer and delivers parasympathetic stimulation only when the measured exertion level is below a specified limit value.

In additional examples, the extent of parasympathetic stimulation varies inversely with measured exertion. For example, in one embodiment, the device measures the patient's cardiac output and delivers parasympathetic stimulation either in proportion to the measured cardiac output or only when the cardiac output exceeds a specified limit value. In another embodiment, measurements of cardiac output and exertion level are combined to provide a composite parameter that indicates the adequacy of the measured cardiac output. In various embodiments, a look-up table is used to match a particular exertion level with a minimum cardiac output considered to be adequate. The device is programmed to deliver parasympathetic stimulation only if cardiac output is at a level considered to be adequate to meet metabolic demand.

FIGS. 1-6 illustrate various embodiments of leads and lead assemblies adapted to deliver neural stimulation and ventricular stimulation. Leads illustrated include at least one electrode capable of delivering an electrical pulse to a patient, and various embodiments include sensors capable of measuring physiological parameters of a patient. Some embodiments can employ, for example, micro-electrical mechanical systems (MEMS) technology to gather physiological data. It should be noted that these illustrations are not drawn to scale, and should not be read as limiting other aspects and embodiments of the present subject matter.

According to various examples used for providing cardiac resynchronization therapy, at least one electrode is placed to stimulate the left ventricle. In various embodiments, the lead for cardiac resynchronization therapy is placed within the coronary sinus, an area which is proximal to parasympathetic ganglia. Parasympathetic ganglia reside in epicardial fat pads, including the fat pad bounded by the left atrium and the inferior vena cava.

The leads illustrated in FIGS. 1-6 include electrodes adapted for stimulation of the ganglia in the fat pad that is proximal to the coronary sinus. In particular, FIGS. 1-3 include transvascular electrodes for stimulation through the wall of the coronary sinus, through various pathways to a vagal nerve proximal the fat pad bounded by the inferior vena cava and the left atrium (IVC-LA fat pad).

Various embodiments of the present subject matter deliver neural stimulation in addition to the cardiac resynchronization therapy in a ventricle, using a common lead. The following examples include embodiments within this scope. These lead illustrations should not be read as limiting other aspects and embodiments of the present subject matter.

FIG. 1 illustrates one embodiment of a lead assembly for implantation of one or more electrodes into a coronary vein on the left side of the heart according to the present subject matter. The lead, in various embodiments, includes a main lead body 102 made of an electrically insulative material. In one embodiment, the lead assembly is shaped like a flexible cylinder. The main lead body 102 includes a proximal portion 101 and a distal portion 120. In various embodiments, one or more lumen extend through the main lead body from approximately the proximal portion 101 to approximately the distal portion 120. In one embodiment, a main lead body lumen extends from a proximal portion 101 to the distal portion and terminates in an opening in a distal end.

In various embodiments, the main lead body 102 is constructed of a polymer surrounding a reinforcement material. Various embodiments include a biocompatible polymer, such as silicone rubber, but other materials are within the scope of the present subject matter. In one embodiment, the reinforcement material is a coiled wire, giving the flexible body rigidity in axial compression, but flexibility when stressed approximately orthogonal to an axis defining the center-line of the lead body. In an embodiment, the coiled wire is used as a conductor in addition to its use as reinforcement material. In various embodiments, the lumen passes through the coiled wire. In some embodiments, the coiled wire includes predetermined bends, resulting in a mechanical bias. For example, in one embodiment, the coiled wire includes a set of bends adapted to assist placement of the main lead body 102 in a coronary sinus, and in some embodiments, other cardiac veins. In some lead embodiments, the insulator itself includes a set of bends adapted to assist placement of the main lead body. In some examples, reinforcement material placed in the distal portion 120 has a bias resulting in a curve such that the distal portion bends in the absence of a guidewire and straightens when a guidewire is placed in the lumen running through the main lead body 102.

According to various embodiments, the main lead body 102 includes a first electrode 104 adapted to stimulate nerves that innervate the heart. Various electrode embodiments include at least one conductive band that at least partially circumscribes the main lead body 102. The first electrode is integrated into the main lead body 102 in some embodiments. For example, some embodiments use an exposed portion of the coil that is used to add axial stiffness to the main lead body 102 as the electrode. Other electrode designs can be used.

In various embodiments, the lead also includes a second lead body slidably disposed in a lumen of the main lead body. A second lead body such as the stimulation element 106 is slidably placed through a lumen of the main lead body 102. In various embodiments, the stimulation element runs from approximately the proximal portion 101 to approximately the distal portion 120, and in one embodiment, from approximately the proximal portion to an opening in the distal end, and through the opening. In one embodiment, the stimulation element is positioned after establishing capture of the heart, and is then fixed in position.

In various embodiments, the stimulation element 106 is a substantially flexible construction adapted for passage through patient vasculature. For example, some embodiments of the stimulation element 106 include a metallic core surrounded by an insulative material. In one example, the stimulation element 106 includes a biocompatible metallic structure including a titanium alloy, the structure being at least partially insulated, e.g. coated or covered, in a polymer. In additional examples, the flexible construction demonstrates a varied number of gradations in cross-sectional area resulting in a gradually varying diameter.

Some examples of the present subject matter stimulate the left ventricle with an electrode placed in a cardiac vein. In various embodiments, the illustrated device includes a second electrode 108 which is adapted for placement proximal the left ventricle, and which is adapted for stimulation of the left ventricle. In some embodiments, the electrode comprises a portion of the stimulation element 106, and in one embodiment, the stimulation element is an insulated wire, with an exposed portion comprising the second electrode 108.

It should be noted that various designs intended to electrically isolate the first electrode 104 from the second electrode 108 are within the scope of the present subject matter. For example, in one embodiment, the first electrode is constructed from a portion of coiled wire, and this coiled wire is electrically insulated in the main lead body 102 both from other lumen(s) and from areas external to the main lead body 102. Additional embodiments of the present subject matter offer added advantages and features. For example, the wall of the lumen is coated with a lubricious coating or a polymer with a low coefficient of friction to reduce friction between a guide wire and the wall of the lumen. Additional lumens can be provided, with some including an additional channel for a guide wire or other apparatus.

Leads made in conformance with the present subject matter are inserted in a number of different ways. For example, a guide catheter is inserted and then the lead passed through the guide catheter until it is properly positioned. The lead is coated with a lubricious coating to reduce friction in the guide catheter. The guide catheter can then be retracted. Additionally, a guide wire is advanced to the implant site alone or through a guide catheter.

Using a lumen, a lead is slid over the guide wire until the lead is properly positioned. For example, the lead is slid until a first electrode is placed in a desired position to capture vagal nerves during stimulation. The guide wire or guide catheters can then be retracted. In embodiments using a stimulation element 106, the stimulation element 106 can take the place of the guide wire, and is left in position for use as a stimulation device for the left ventricle.

Also, a lead is temporarily fixed to a guide catheter. The fixate is designed to dissolve in body fluids. The lead can then be inserted along with the guide catheter. After the electrode is in place and the fixate dissolves, the guide catheter is retracted. It should be noted that modern techniques, including modern angiography techniques, fall within the scope of the present subject.

Figure 2:
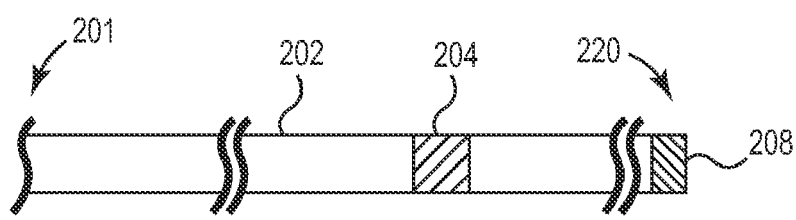
FIG. 2 shows a lead adapted to deliver neural stimulation and ventricular stimulation, according to various embodiments of the present subject matter.

FIG. 2 illustrates one embodiment of a lead for implantation of an electrode into a coronary vein on the left side of the heart. In various embodiments, the lead includes a main lead body 202, with a proximal portion 201, and a distal portion 220. The lead also includes a first electrode 204 and a second electrode 208. The first electrode 204, in various embodiments, is integrated into the main lead body 202, and in additional embodiments, includes features for transvascular stimulation of parasympathetic ganglia located in the IVC-LA fat pad. In one example, the first electrode 204 is a conductive band at least partially circumscribing the main lead body 202.

The second electrode 208, in various embodiments, is also integrated into the main lead body 202. In various embodiments, the second electrode 208 includes features adapted to stimulate the left ventricle. In some examples, the second electrode 208 includes a tip having features compatible with tissue growth. For example, in one embodiment the second electrode includes a porous screen which is adapted to foster connection through fibrous growth of myocardial tissue into the pores. In one embodiment the porous screen is made from platinum iridium, however, other materials include diamond, iridium oxide, titanium nitride, titanium oxide, platinum, titanium, and tantalum.

In various embodiments, the first electrode and the second electrode are electrically isolated from each other. In some examples, the first integrated electrode 204 comprises an exposed portion of a conductive coil running the length of the main lead body 202. In these examples, the second electrode is connected either with a secondary coaxial coil, or with a conductor. It should be noted that various embodiments, however, include multiple conductors running through portion of the main lead body 202 which provide electrical communication paths between the electrodes and the proximal portion 201. In one embodiment, a pair of cables extend through portions of the main lead body 202 and provide circuits capable of connecting the first electrode and the second electrode to terminals located at the proximal portion of the main lead body 202. In an additional embodiment, cables extend through portions of a lumen located in the main lead body 202. In one embodiment, the lumen for conductor passage is coated with a lubricant, including biocompatible electrically resistant lubricants.

In various embodiments, the main lead body 202 includes a lumen for a wire, such as a stylet, a guidewire, or a pushwire. In various embodiments, the guidewire is adapted to add rigidity to the main lead body 202 when bending along an axis orthogonal to a centerline coaxial to the length of the main lead body. However, various guidewires are used, adding various levels of rigidity. Additionally, one or more coils disposed in the main lead body can include a mechanical bias, and the slidable placement of the guidewire within a lumen can temporarily remove the mechanical bias for implantation steps. Upon successful implantation, the guidewire is removed, restoring a mechanical bias. In various embodiments, a mechanical bias is useful for adapting the lead to the patient's physiology, including moving one or more conductors into improved electrical communication with aspects of patient physiology.

It should also be noted that the distal end 220 of the main lead body 202 can feature an opening for lumen termination. In these examples, the lead is implanted using over-the-wire methodology, rather than stylet methodology. However, each embodiment is within the scope of the present subject matter, and additional embodiments not enumerated here also fall within the present scope. Modern lead deployment practices are increasingly varied, and the present subject matter is suited for implantation using these methods.

Figure 3:
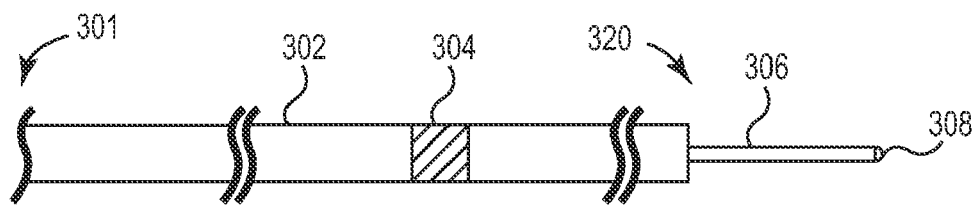
FIG. 3 shows a lead adapted to deliver neural stimulation and ventricular stimulation, according to various embodiments of the present subject matter.

FIG. 3 illustrates one embodiment of a lead for implantation of an electrode into a coronary vein on the left side of the heart. In various embodiments, the lead includes a first main lead body 302, which includes a proximal portion 301 and a distal portion 320. In various embodiments, the lead is constructed out of materials such as those in the discussion associated with the illustrations of FIGS. 1-2.

The lead includes, in various embodiments, lumen extending through the main lead body 302. In various embodiments, the lumen terminates in an opening in the distal end. Various aspects of the present subject matter include, but are not limited to, a lumen which has a diameter sized to slidably receive a second lead body 306. In various embodiments, the second lead body includes an integrated second electrode 308, adapted for stimulation of the left ventricle. Also, the second lead body contains one or more lumen adapted to slidably contain varied apparatus such as a guidewire.

In various embodiments, the main lead body 302 includes a lumen adapted to slidably receive a guidewire in addition to a second lead body. However, various embodiments of the present subject matter benefit from a second lead body 306 which can act as a guidewire. In various embodiments, the second lead body 306 is a polymeric material stiffened with a reinforcing material. In one example, the second lead body 306 is a cylindrical elongate portion of silicone rubber stiffened with a coiled metallic structure. In some embodiments, the second lead body 306 is stiffened in axial compression and not bending, but other embodiments are within the scope of the present subject matter. Various embodiments of the second lead body 306 also include a mechanical bias.

In various embodiments, the second lead body includes a lumen adapted to slidably receive a guidewire. During insertion of the lead into a patient, the guidewire combined with the second lead body 306 provides stiffness adequate to manipulate mechanical bias incorporated into the design of reinforcement material for the main lead body 302. For example, by first inserting a guidewire into the second lead body 306, and then inserting the combined guidewire and second lead body into the main lead body 302, one can use a curve shaped mechanical bias located at the distal portion 320 of the main lead body 302 to tune the approach angle of the distal portion as it is moved through vasculature.

Once the first electrode 304 is positioned in a satisfactory location for transvascular stimulation of epicardial ganglia in the IVC-LA fat pad, the second lead body 306 is extended into cardiac vasculature, and positioned for stimulation of a left ventricle. The approach angle of the second lead body 306 is adjusted with the addition or removal of a guidewire to allow or reduce various degrees of a mechanical bias located proximal the tip of the second lead body 306. After the positioning of the second lead body 306, the guidewire is either extended beyond the tip of the second lead body, for use as a stimulation element, as a physiological information sensor, or as a physiological information transceiver. However, in additional embodiments, the guidewire is retracted. In some embodiments, the second lead body 306 does not include an opening in a distal portion through which a guidewire can extend.

Various methods are useful to indefinitely fix the main lead body 302 to the second lead body 306. In some embodiments, the main lead body 302 and the second lead body 306 are formed into a terminal at the proximal portion of the main lead assembly.

Figure 4:
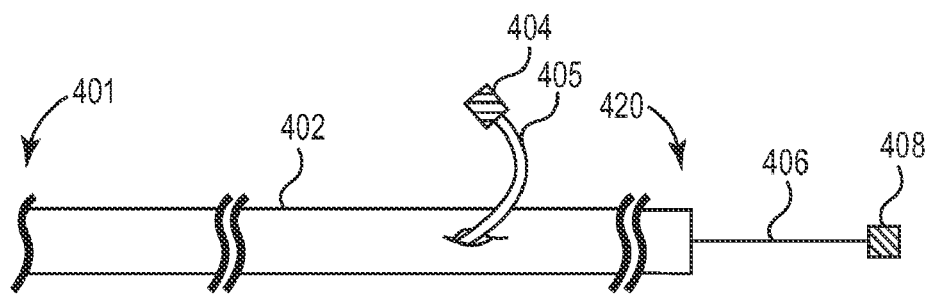
FIG. 4 shows a lead adapted to deliver neural stimulation, according to various embodiments of the present subject matter.
Figure 5:
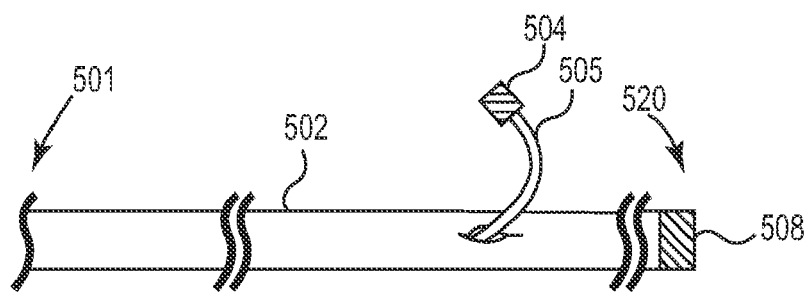
FIG. 5 shows a lead adapted to deliver neural stimulation, according to various embodiments of the present subject matter.
Figure 6:
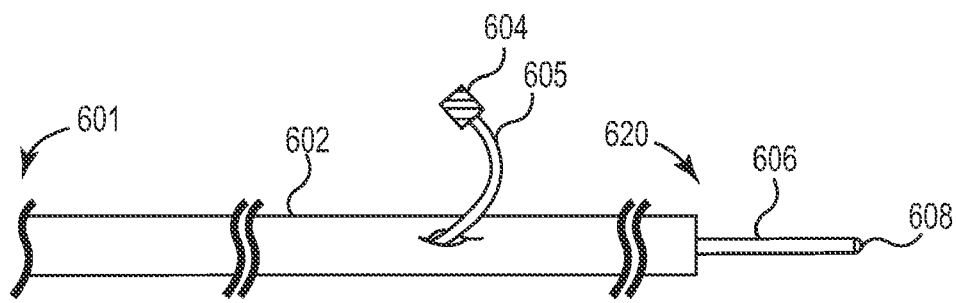
FIG. 6 shows a lead adapted to deliver neural stimulation, according to various embodiments of the present subject matter.

Due to the proximity of epicardial ganglia to the coronary sinus, the leads illustrated in FIGS. 4-6 include electrodes adapted for puncturing vasculature and entering the IVC-LA fat pad. The electrodes are adapted for stimulation of parasympathetic ganglia located in the IVC-LA fat pad. Various embodiments of the present subject matter deliver a neural stimulation at or near the IVC-LA fat pad in addition to the cardiac resynchronization therapy in a ventricle, using a common lead. The following examples include embodiments within this scope. It should be noted, however, that these lead illustrations should not be read as limiting other aspects and embodiments of the present subject matter.

FIG. 4 illustrates a lead adapted for implantation and delivery of neural stimulation and cardiac resynchronization therapy, according to one embodiment of the present subject matter. In various embodiments, at least two lumen extend through the main lead body from approximately the proximal portion 401 to approximately the distal portion 420.

In one embodiment, a first lumen extends to the distal portion and terminates in an opening at the distal end. In various embodiments, the lead includes a stimulation element 406 slidably placed through the first lumen in the main lead body 402. In various embodiments, the stimulation element runs from approximately the proximal portion 401 of the main lead body 402 to approximately the distal portion 420 of the main lead body 402, and in one embodiment, from approximately the proximal portion of the main lead body 402 to an opening in the distal portion, and through the opening. In various embodiments, the stimulation element 406 is integrated with a second electrode 408, including aspects discussed in the teachings of FIG. 1, however aspects of the present subject matter which are not discussed in the teachings associated with that figure additionally fall within the scope of the present subject matter. The stimulation element 406, in various embodiments, is positioned in a venous branch draining into the coronary sinus, and is adapted to stimulate the left ventricle.

Additionally, in various embodiments, the main lead body 402 includes a puncture body lumen adapted to receive a steerable extravascular lead body 405. In various embodiments, the steerable extravascular lead body 405 includes an electrode 404. In various embodiments, the steerable extravascular lead body 405 and electrode 404 are adapted to puncture tissue, and place the electrode 404 into electrical communication with autonomic ganglia at or near the IVC-LA fat pad. Various aspects of a steerable extravascular lead body 405 and the electrode 404, are discussed in the teachings associated with FIG. 11, however, aspects of the present subject matter which are not discussed in the teachings associated with that figure additionally fall within the scope of the present subject matter.

FIG. 5 illustrates a lead adapted for implantation and delivery of neural stimulation and cardiac resynchronization therapy, according to one embodiment of the present subject matter. In various embodiments, the lead includes a main lead body 502, with a proximal end 501 and a distal end 520. In one embodiment, the main lead body 502 is integrated with a second electrode 508, including structural aspects discussed in the teachings of FIG. 2, however aspects of the present subject matter which are not discussed in the teachings associated with that figure additionally fall within the scope of the present subject matter.

Additionally, in various embodiments, the main lead body 502 includes features adapted for positioning an electrode at or near the IVC-LA fat pad. For example, in one embodiment, the main lead body 502 includes a lumen adapted to receive a steerable extravascular lead body 505. In various embodiments, the steerable extravascular lead body 505 includes an electrode 504. In various embodiments, the steerable extravascular lead body 505 and electrode 504 are adapted to puncture tissue. Various aspects of a steerable extravascular lead body 505 and an electrode 504, the combination adapted for puncturing tissue, are discussed in the teachings associated with FIG. 11; however aspects of the present subject matter which are not discussed in the teachings associated with that figure additionally fall within the scope of the present subject matter.

FIG. 6 illustrates a lead adapted for implantation and delivery of neural stimulation and cardiac resynchronization therapy, according to one embodiment of the present subject matter. In various embodiments, at least two lumen extend through the main lead body from approximately the proximal portion 601 to approximately the distal portion 620.

In one embodiment, a first lumen extends to the distal portion and terminates in an opening at the distal end. In various embodiments, the lead includes a second lead body 606 slidably disposed in the first lumen of the main lead body 602. For example, the second lead body is composed of a polymer stiffened by a reinforcing material, for example, silicone rubber containing a coiled metallic element. Additionally, the second lead body 606 includes a third lumen, which, in various embodiments, is adapted to slidably receive a guidewire.

In various embodiments, the second lead body 606 runs from approximately the proximal portion 601 of the main lead body 602, to approximately the distal portion 620, and in one embodiment, from approximately the proximal portion 601 of the main lead body 602 to an opening in the distal end of the main lead body 602, and through the opening. In various embodiments, the second lead body 606 is integrated with a second electrode 608, including aspects discussed in the teachings of FIG. 3, however aspects of the present subject matter which are not discussed in the teachings associated with that figure additionally fall within the scope of the present subject matter. The second lead body 606, in various embodiments, is positioned in a cardiac vein draining into the coronary sinus, and is adapted to position the second electrode 608 for stimulation of the left ventricle.

Additionally, in various embodiments, the main lead body 602 includes a lumen adapted to receive a steerable extravascular lead body 605. In various embodiments, the steerable extravascular lead body 605 includes an electrode 604. In various embodiments, the steerable extravascular lead body 605 and electrode 604 are adapted to puncture tissue, and are additionally adapted to place the electrode 604 into electrical communication with autonomic ganglia in the IVC-LA fat pad. Various aspects of a steerable extravascular lead body 605 and the electrode 604 are discussed in the teachings associated with FIG. 11, however aspects of the present subject matter which are not discussed in the teachings associated with that figure additionally fall within the scope of the present subject matter.

Figure 7:
FIG. 7 shows a lead with a lead for transvascular stimulation, according to various embodiments of the present subject matter.

FIG. 7 shows a lead assembly adapted to deliver neural stimulation with a ring electrode, and ventricular stimulation with a tip electrode, according to various embodiments of the present subject matter. Various embodiments of the lead illustrated include aspects of the lead discussed in FIG. 2, however aspects of the present subject matter which are not discussed in the teachings associated with that figure additionally fall within the scope of the present subject matter.

In various embodiments, the lead includes a main lead body 704 constructed from a biocompatible material, and including a rigidity adapted for placement in vasculature. In various embodiments, the lead includes a ring electrode 702. In various embodiments, the ring electrode structure includes at least one conductive band at least partially circumscribing the main lead body. In various embodiments, the ring electrode includes one or more regions placed in electrical communication with one or more conductors running through the main lead body 704 to a terminal suitable for connection to an implantable cardiac rhythm management device.

In various embodiments, the ring electrode 702 includes an exposed metallic surface connected to the metallic coil which runs the length of the main lead body 704. Additionally, the lead includes a tip 706 adapted for providing an electrical pulse to a patient. In particular, the main lead body 704 is sized to place the electrodes 702 proximal the IVC-LA fat pad, and, additionally, to place electrode 706 proximal the left ventricle, typically in a cardiac vein, the electrode 706 positioned to deliver ventricular stimulation.

Figure 8:
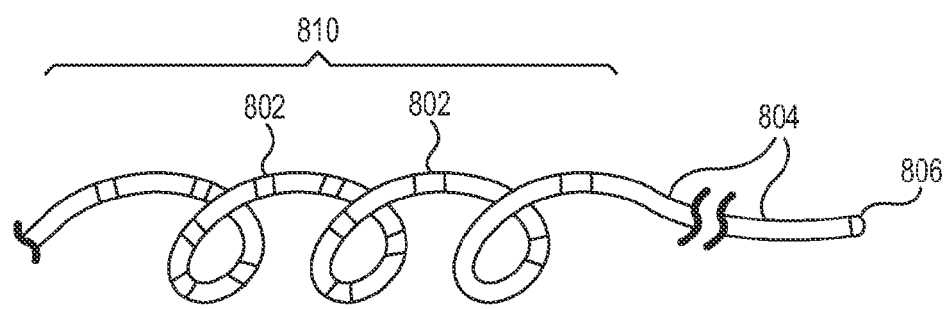
FIG. 8 shows a lead with a lead for transvascular stimulation, according to various embodiments of the present subject matter.

FIG. 8 shows a series of ring electrodes adapted to deliver neural stimulation combined with a lead with a mechanical bias, and a tip electrode adapted to deliver ventricular stimulation, according to one embodiment of the present subject matter. The mechanical bias illustrated is helical in shape, but other shapes are within the scope of the present subject matter. Various embodiments of the lead illustrated include aspects of the lead discussed in FIG. 2, however aspects of the present subject matter which are not discussed in the teachings associated with that figure additionally fall within the scope of the present subject matter.

In various embodiments, the lead includes a mechanical bias 810 resulting in a helix shape. The bias is relieved by the insertion of a guidewire, in various embodiments of the present subject matter. The bias is useful for positioning the lead in vasculature. For example, in one embodiment, the outer diameter of the helix shape is sized to mate to the inner diameter of the coronary sinus proximal the IVC-LA fat pad, and the bias aids in putting one or more electrodes 802 in electrically communication with the patient vasculature.

One feature present in some embodiments is an array of electrodes. In various embodiments, the electrodes include individually wired elements capable of individually delivering an electronic pulse. In various embodiments, each individual element is in electrical communication with an individual terminal, typically positioned near a proximal portion, and suited for connection to an implantable pulse generator. By using an array of electrodes, rather than a single electrode, transvascular stimulation is more effective. For example, a physician can tune the bias 810 to deliver an improved form of neural stimulation by adjusting the energy delivered to several regions of the electrodes 802.

Additionally, the lead includes a tip 806 adapted for providing an electrical pulse to a patient. In particular, the main lead body 804 is sized to place the electrodes 802 proximal the IVC-LA fat pad, and, additionally, to place electrode 806 proximal the left ventricle, such as in a cardiac vein. The electrode 806 positioned to deliver ventricular stimulation.

Helical electrodes within the scope of the present subject matter include those taught in the following commonly assigned U.S. patent is related and incorporated herein by reference: "Leads for Pacing and/or Sensing the Heart from Within the Coronary Veins," U.S. Pat. No. 6,584,362, filed Aug. 30, 2000, issued Jun. 24, 2003.

Figure 9:
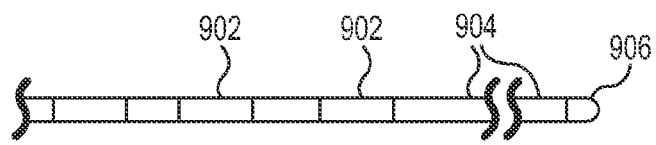
FIG. 9 shows a lead with at least one ring electrode adapted to deliver neural stimulation, and a tip electrode adapted to deliver ventricular stimulation, according to various embodiments of the present subject matter.

FIG. 9 shows a lead with at least one ring electrode 902 adapted to deliver neural stimulation, and a tip electrode adapted to deliver ventricular stimulation, according to various embodiments of the present subject matter. Various embodiments include aspects of the lead discussed in FIG. 8.

The lead illustrates one example of a lead with one or more electrode sites 902 for stimulation of parasympathetic ganglia in the IVC-LA fat pad. Additionally, the example illustrates electrode sites 902 integrated with a main lead body 904, and also illustrates one embodiment of a lead without a mechanical bias.

The lead additionally includes a tip 906 adapted for providing an electrical pulse to a patient. In particular, the main lead body 904 is sized to place the electrodes 902 proximal the IVC-LA fat pad, and, additionally, to place electrode 906 proximal the left ventricle, typically in a cardiac vein, the electrode 906 positioned to deliver ventricular stimulation.

Figure 10:
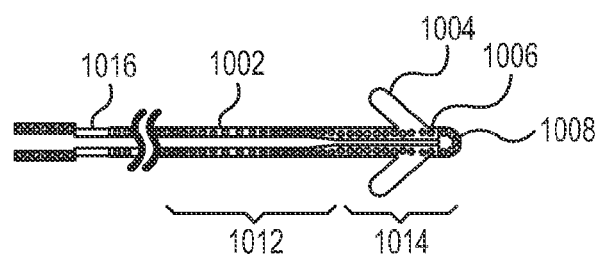
FIG. 10 shows a lead with at least one ring electrode adapted to deliver neural stimulation, and a tip electrode adapted to deliver ventricular stimulation, according to various embodiments of the present subject matter.

FIG. 10 shows a partial cross section of a lead with at least one ring electrode adapted to deliver neural stimulation, and a tip electrode adapted to deliver ventricular stimulation, according to various embodiments of the present subject matter. Various embodiments of the illustrated lead include aspects of the lead discussed in FIG. 2, however aspects of the present subject matter which are not discussed in the teachings associated with that figure additionally fall within the scope of the present subject matter.

The lead includes a ring electrode 1016, adapted for providing electrical stimulation to parasympathetic ganglia located in the IVC-LA fat pad. Additionally, the lead includes a tip suitable for implantation proximal the left ventricle. In particular, the lead includes a reinforcement element 1006 adapted to be deformed to be implanted in a cardiac vein. The lead can include a mechanical bias, and various embodiments include a curve which assists in placement of the lead in vasculature.

For example, in one embodiment, the lead includes a guidewire 1002 of various diameters, including a thicker portion 1012, a thinner portion 1014, and a taper disposed between the two portions. In various embodiments, by positioning the guidewire in different places relevant to the reinforcing element 1006, one can manipulate the lead for vascular implantation.

In various embodiments, the lead additionally includes tines 1004 and a tip 1008 which are adapted for fostering tissue growth, the new tissue serving to anchor the lead into position.

Figure 11:
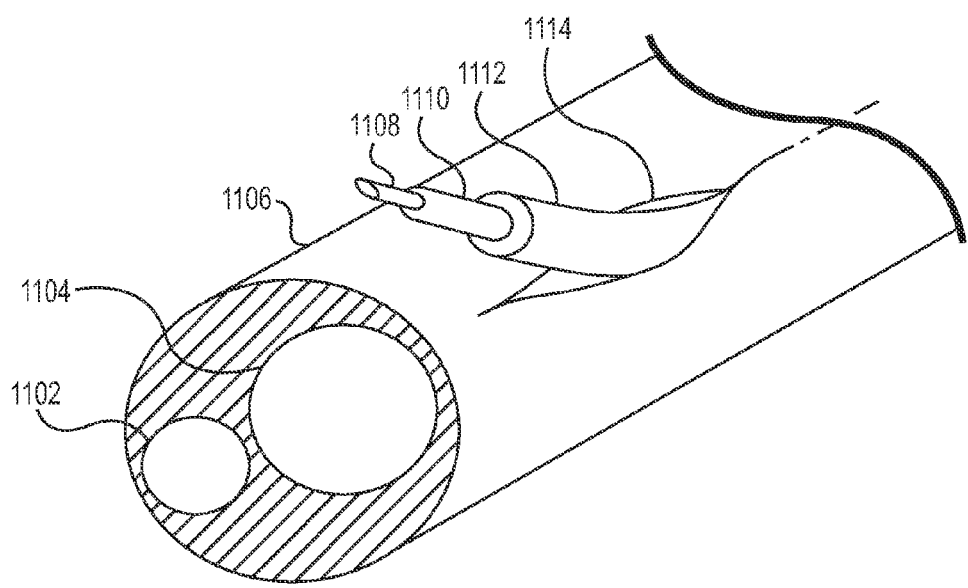
FIG. 11 shows a perspective view including a partial cross section of a lead, according to one embodiment of the present subject matter.

FIG. 11 shows a perspective view including a cross section of a lead adapted to deliver neural stimulation using at least one electrode for puncturing vasculature, according to one embodiment of the present subject matter.

In various embodiments, the lead includes a main lead body 1106. The main lead body 1106 includes, in various embodiments, a puncture body lumen 1104 adapted for passage of a steerable extravascular lead body, and a second lumen 1102 adapted for passage of a guidewire, stylet or cardiac resynchronization therapy lead. In various embodiments, the main lead body 1106 is made from a resilient material, such as silicon rubber, which, in some examples, has a rigid reinforcing material.

The steerable extravascular lead body 1112, in various embodiments, includes several aspects useful for puncturing tissue, and in particular, vasculature. In one embodiment, the steerable extravascular lead body includes an elongate cylindrical portion which is cut at an angle, providing a sharpened edge adapted to puncture tissue.

The steerable extravascular lead body additionally includes aspects which are helpful for placing an implantable pulse generator connected to a lead into electrical communication with autonomic ganglia, and in particular, ganglia present in the IVC-LA fat pad. For example, in some embodiments, the steerable extravascular lead body 1112 is disposed in the puncture body lumen 1104. The steerable extravascular lead body 1112, in various embodiments, is a polymeric material which either is sufficiently stiff to enable the steerable extravascular lead body 1112 to burst through the walls defining the puncture body lumen 1104 to the exterior of the main lead body 1106, or is reinforced. For example, in one embodiment, the steerable extravascular lead body 1112 includes a reinforcing material including a mechanical bias, which forces the steerable extravascular lead body 1112 into a curve, and out of axial alignment with the puncture body lumen 1104. In one embodiment, the strength of the mechanical bias is selected to enable the steerable extravascular lead body 1112 to burst through the wall of the puncture body lumen 1104. Additionally, the mechanical bias is manipulated so as to enable straightening when combined with a guidewire or other element suitable for guiding the main body through vasculature. Alternatively, the lead body 1106 could be manipulated using a bias and guidewire in lumen 1102 to create a corner around which extravascular lead 112 would not follow, but exit lumen 1104.

For example, in one embodiment, the extravascular lead body 1112 includes a lumen. Straightening the extravascular lead body 1112, in various embodiments, is accomplished by inserting one or more components into the lumen. In one embodiment, a probe 1108 is inserted. The probe, in various embodiments, is a conductive member adapted for electrical communication with parasympathetic ganglia located in the IVC-LA fat pad. The probe 1108 can include a tapered tip with a sharp apex, adapted to puncture tissue. The probe, as such, is useful for puncturing tissue after the steerable extravascular lead body 1112 has punctured the puncture body lumen 1104.

Phrased otherwise, in one embodiment, the steerable extravascular lead body 1112 includes a bias forming a curvature. During implantation, a probe 1108 is inserted to straighten the bias. The steerable extravascular lead body 1112 is then positioned in a first position, disposed in the main lead body 1106 in a location which is desirable for puncturing tissue and placing an electrode in electrical communication with parasympathetic ganglia located in the IVC-LA fat pad. In a second position, the probe is removed, restoring the bias in steerable extravascular lead body 1112, the bias being of a sufficient strength to puncture the wall of the puncture body lumen 1104 in the main lead body 1106, the probe 1108 then being reinserted and put into electrical communication with parasympathetic ganglia of the IVC-LA fat pad.

Positioning the probe, however, is further improved by using a second body 1110, which, in various embodiment, can include a secondary bias. In various embodiments, once the steerable extravascular lead body 1112 punctures the walls of the puncture body lumen 1104, reinsertion of elements internal to the steerable extravascular lead body 1112 tends to introduce forces which urge the steerable extravascular lead body 1112 back into coaxial alignment with the puncture body lumen 1104. One way to reduce the effect of this tendency is to use probe 1108 and a secondary body 1110. For example, in one embodiment, a guidewire of a high stiffness is used to initially extend the main body into position, and then to release the main body bias. In various embodiments, the main body punctures the puncture body lumen 1104 of the main lead body 1106. The lumen through which the guidewire passed is filled with the combined probe 1108 and secondary body 1110, in various embodiments. In one example, the combined probe and secondary body is less stiff than the guidewire.

In various embodiments, the secondary body includes a bias, and the probe serves to eliminate the bias during implantation. By changing the location of the probe within the secondary body, various degrees of approach angle to tissue is achieved, resulting in a secondary body which is directed through tissue. In some examples, combining the bias of the main body and the secondary body enables one to obtain improved maneuverability with respect to the final positioning of the probe 1108.

In various embodiments, the lead includes aspects which promote vascular healing after puncture. For example, in one embodiment, a portion of the steerable extravascular lead body includes extracellular matrix (ECM). ECM includes decellularized xenogeneic or allogeneic isolated ECM, e.g., ECM isolated from small intestinal submucosa. The term "isolated" when used in relation to ECM, refers to a complex of molecules that is identified and/or separated from at least one contaminant biological component with which it is ordinarily associated in its natural source. Isolated ECM is present in a form or setting that is different from that in which it is found in nature.

Isolated ECM is a unique biomaterial with unique properties, e.g., isolated ECM is biocompatible, e.g., has low immunogenicity, biodegradable, anti-thrombotic, anti-inflammatory and/or anti-bacterial, and optionally has mechanical and regenerative properties, e.g., the modulation of fibrosis, promotion of cell infiltration, or promotion of deposition of host derived neomatrix. Thus, when ECM is used with an implanted device, the performance of that device may be improved. For example, when ECM is used as an external interface layer between a patient and an implanted device such as a lead, the chronic performance and patient tolerance of these devices may be improved.

ECM may be isolated from endothelial layers of various cell populations, tissues and/or organs. In one embodiment, ECM is isolated from any organ or tissue source including the dermis of the skin, liver, alimentary, respiratory, intestinal, urinary or genital tracks of a warm blooded vertebrate. ECM employed in the invention may be from a combination of sources. Isolated ECM may be prepared as a sheet, in particulate form, gel form and the like.

In one embodiment, ECM is isolated from the small intestine. Intestinal submucosal tissue for use in the invention typically comprises the tunica submucosa delaminated from both the tunica muscularis and at least the luminal portions of the tunica mucosa. In one embodiment, the submucosal tissue comprises the tunica submucosa and basilar portions of the tunica mucosa including the lamina muscularis mucosa and the stratum compactum. The preparation of submucosal tissue is described in U.S. Pat. No. 4,902,508 and Bell, In: *Tissue Engineering: Current Perspectives*, Cambridge, Mass., Burkhauser Publishers, pp. 179-189 (1993), the disclosures of which are expressly incorporated herein by reference. For example, a segment of vertebrate intestine, preferably harvested from porcine, ovine or bovine species, or other warm blooded vertebrates, is rinsed free of contents, then split longitudinally to form a sheet and delaminated. In particular, the superficial layers of the tunica mucosa are removed by mechanical delamination. The tissue is then turned to the opposite side and the tunica muscularis externa and tunica serosa are mechanically removed leaving the tunica submucosa and the basilar layers of the tunica mucosa. The remaining tissue represents isolated ECM and may include a small number of intact cells.

In one embodiment, ECM is isolated from the urinary bladder. The wall of the urinary bladder is composed of the following layers: the mucosa (including a transitional epithelium layer and the tunica propria), a submucosa layer, up to three layers of muscle and the adventitia (a loose connective tissue layer)—listed in crossection from luminal to albuminal sides. Urinary bladder submucosa may be prepared from bladder tissue harvested from animals raised for meat production, including, for example, porcine, ovine or bovine species or other warm-blooded vertebrates. For example, the urinary bladder is harvested and thoroughly rinsed in tap water to remove its contents. The bladder is split open through the apex and bisected to yield roughly equal-sized halves that are prepared separately. The luminal side of the bladder is placed face down and the external muscle layers, i.e., muscularis externa (smooth muscle cell layers and serosa), are removed by mechanical delamination. The transitional epithelium of the urinary bladder is removed by either mechanical or ionic methods (e.g., 1.0 N NaCl treatment) leaving behind tissue corresponding to isolated ECM, e.g., approximately a 50 μM to 80 μM thick sheet of ECM that originally resides between the transitional epithelium and the smooth muscle layers of the urinary bladder, i.e., the submucosa and basement membrane of the transitional epithelium.

In another embodiment, ECM from bladder wall segments or small intestine is prepared using a modification to the technique in Meezan et al. (*Life Sci.*, 17:1721 (1975)). The method in Meezan et al. includes placing tissue fractions in a large volume (100:1) of distilled water containing 0.1% sodium azide and magnetically stirring the mixture for 1-2 hours in order to lyse the cells and release the intracellular contents. The lysed tissue suspension is then centrifuged to yield a firm pellet, and the supernatant discarded. The pellet is suspended in 40 ml of 1M NaCl and 2000 Kunitz units of DNAase (Sigma, Deoxyribonuclease 1) are added and the suspension stirred for 1-2 hours. The mixture is again centrifuged to bring down a firm pellet and the supernatant discarded. The pellet is then suspended in 40 ml of 4% sodium deoxycholate containing 0.1% sodium azide and stirred for 2-4 hours at room temperature. The mixture is centrifuged, the supernatant discarded, and the pellet either washed several times with water by centrifugation and resuspension, or by extensive irrigation on a 44 micron nylon sieve (Kressilk Products, Inc., Monterey Park, Calif.). In the modified method, the time of incubation with sodium deoxycholate and sodium azide is increased and additional washing procedures incorporated. Accordingly, first, the mucosa is scraped off mechanically. Afterwards all cell structures of the remaining tissue are eliminated chemically and enzymatically leaving the acellularized muscularis layer. This is achieved with subsequent exposure to a hypoosmolar and hyperosmolar solutions of crystalloids. In addition, a final treatment with sodium deoxycholate destroys remaining cell structures. After following washing procedures, the resulting material, which provides cross-linked fibres of the submucosa with the remaining muscularis collagen-elastin framework, is stored in PBS solution, e.g., with antibiotics at 4° C. for a few months. Isolated ECM is cut, rolled, or folded.

Fluidized forms of submucosal tissue are prepared by comminuting submucosa tissue by tearing, cutting, grinding, or shearing the harvested submucosal tissue. Thus, pieces of submucosal tissue are comminuted by shearing in a high speed blender, or by grinding the submucosa in a frozen or freeze-dried state, to produce a powder that can thereafter be hydrated with water or buffered saline to form a submucosal fluid of liquid, gel or paste-like consistency.

The comminuted submucosa formulation can further be treated with an enzymatic composition to provide a homogenous solution of partially solubilized submucosa. The enzymatic composition may comprise one or more enzymes that are capable of breaking the covalent bonds of the structural components of the submucosal tissue. For example, the comminuted submucosal tissue is treated with a collagenase, glycosaminoglycanase, or a protease, such as trypsin or pepsin at an acidic pH, for a period of time sufficient to solubilize all or a portion of the submucosal tissue protein components. After treating the comminuted submucosa formulation with the enzymatic composition, the tissue is optionally filtered to provide a homogenous solution. The viscosity of fluidized submucosa for use in accordance with this invention is manipulated by controlling the concentration of the submucosa component and the degree of hydration. The viscosity is adjusted to a range of about 2 to about 300,000 cps at 25° C. Higher viscosity formulations, for example, gels, are prepared from the submucosa digest solutions by adjusting the pH of such solutions to about 6.0 to about 7.0.

The present invention also contemplates the use of powder forms of submucosal tissues. In one embodiment, a powder form of submucosal tissue is prepared by pulverizing intestinal submucosa tissue under liquid nitrogen to produce particles ranging in size from 0.01 to 1 mm2 in their largest dimension. The particulate composition is then lyophilized overnight, pulverized again and optionally sterilized to form a substantially anhydrous particulate composite. Alternatively, a powder form of submucosal tissue is formed from fluidized submucosal tissue by drying the suspensions or solutions of comminuted submucosal tissue.

Submucosal tissue may be "conditioned" to alter the viscoelastic properties of the submucosal tissue. Submucosal tissue is conditioned by stretching, chemically treating, enzymatically treating or exposing the tissue to other environmental factors. The conditioning of submucosal tissue is described in U.S. Pat. No. 5,275,826, the disclosure of which is expressly incorporated herein by reference. In accordance with one embodiment, vertebrate derived submucosal tissues are conditioned to a strain of no more than about 20%.

In one embodiment, the submucosal tissue is conditioned by stretching the tissue longitudinally. One method of "conditioning" the tissue by stretching involves application of a given load to the submucosa for three to five cycles. Each cycle consists of applying a load to the tissue for five seconds, followed by a ten second relaxation phase. Three to five cycles produces a stretch-conditioned material. For example, submucosal tissue is conditioned by suspending a weight from the tissue, for a period of time sufficient to allow about 10 to 20% or more elongation of the tissue segment. Optionally, the material is preconditioned by stretching in the lateral dimension.

In one embodiment the submucosal tissue is stretched using 50% of the predicted ultimate load. The "ultimate load" is the maximum load that is applied to the submucosal tissue without resulting in failure of the tissue (i.e., the break point of the tissue). Ultimate load is predicted for a given strip of submucosal tissue based on the source and thickness of the material. Accordingly, one method of "conditioning" the tissue by stretching involves application of 50% of the predicted ultimate load to the submucosa for three to ten cycles. Each cycle consists of applying a load to the material for five seconds, followed by a ten second relaxation phase. The resulting conditioned submucosal tissue has a strain of less than 30%, more typically a strain from about 20% to about 28%. In one embodiment, conditioned the submucosal tissue has a strain of no more than 20%. The term strain as used herein refers to the maximum amount of tissue elongation before failure of the tissue, when the tissue is stretched under an applied load. Strain is expressed as a percentage of the length of the tissue before loading.

Typically the conditioned submucosal tissue is immobilized by clamping, suturing, stapling, gluing (or other tissue immobilizing techniques) the tissue to the support, wherein the tissue is held at its preconditioned length in at least one dimension. In one embodiment, delaminated submucosa is conditioned to have a width and length longer than the original delaminated tissue and the conditioned length and width of the tissue is maintained by immobilizing the submucosa on a support. The support-held conditioned submucosal tissue is sterilized before or after being packaged.

Preferably, isolated ECM is decellularized, and optionally sterilized, prior to storage and/or use. In one embodiment, isolated ECM has a thickness of about 50 to 250 micrometers, e.g., 100 to 200 micrometers, and is >98% acellular. Numerous methods may be used to decellularize isolated ECM (see, for example, Courtman et al., *J. Biomed. Materi. Res.*, 18:655 (1994); Curtil et al., *Cryobiology*, 34:13 (1997); Livesey et al., *Workshop on Prosthetic Heart Valves*, Georgia Inst. Tech. (1998); Bader et al., *Eur. J. Cardiothorac. Surg.*, 14:279 (1998)). For instance, treatment of isolated ECM with dilute (0.1%) peracetic acid and rinsing with buffered saline (pH 7.0 to 7.4) and deionized water renders the material acellular with a neutral pH. Alternatively, isolated ECM is thoroughly rinsed under running water to lyse the remaining resident cells, disinfected using 0.1% peracetic acid in ethanol, and rinsed in phosphate buffered saline (PBS, pH=7.4) and distilled water to return its pH to approximately 7.0. Decellularization may be ascertained by hematoxylin-eosin staining.

Isolated, and optionally decellularized, ECM contains a mixture of structural and functional molecules such as collagen type I, III, IV, V, VI; proteoglycans; glycoproteins; glycosaminoglycans; and growth factors in their native 3-dimensional microarchitecture, including proteins that influence cell attachment, gene expression patterns, and the differentiation of cells. Isolated ECM is optionally sterilized and may be stored in a hydrated or dehydrated state.

Isolated ECM may be sterilized using conventional sterilization techniques including tanning with glutaraldehyde, formaldehyde tanning at acidic pH, ethylene oxide treatment, propylene oxide treatment, gas plasma sterilization, gamma radiation, electric beam radiation and peracetic acid sterilization. Sterilization techniques which do not adversely affect the mechanical strength, structure, and biotropic properties of the isolated ECM are preferred. For instance, strong gamma radiation may cause loss of strength of sheets of submucosal tissue. Preferred sterilization techniques include exposing isolated ECM to peracetic acid, low dose gamma irradiation, e.g., 1-4 mRads gamma irradiation or more preferably 1-2.5 mRads of gamma irradiation, or gas plasma sterilization. In one embodiment, peracetic acid treatment is typically conducted at a pH of about 2 to about 5 in an aqueous ethanolic solution (about 2 to about 10% ethanol by volume) at a peracid concentration of about 0.03 to about 0.5% by volume. After isolated ECM is sterilized, it may be wrapped in a porous plastic wrap or foil and sterilized again, e.g., using electron beam or gamma irradiation sterilization techniques. Isolated ECM for implantation is generally subjected to two or more sterilization processes. Terminal sterilization, e.g., with 2.5 mRad (10 kGy) gamma irradiation results in a sterile, pyrogen-free biomaterial. Isolated ECM or isolated, decellularized ECM may then be stored, e.g., at 4° C., until use. Lyophilized or air dried ECM is rehydrated and used in accordance with this invention without significant loss of its properties. Decellularized and/or sterilized isolated ECM is substantially nonimmunogenic and has high tensile strength. Isolated ECM may, upon implantation, undergo remodeling (resorption and replacement with autogenous differentiated tissue), serve as a rapidly vascularized matrix for support and growth of new tissue, and assume the characterizing features of the tissue(s) with which it is associated at the site of implantation, which may include functional tissue.

In some embodiments, isolated ECM may be subjected to chemical and non-chemical means of cross-linking to modify the physical, mechanical or immunogenic properties of naturally derived ECM (Bellamkondra et al., *J. Biomed. Mater. Res.*, 29:633 (1995)). Chemical cross-linking methods generally involve aldehyde or carbodiimide. Photochemical means of protein cross-linking may also be employed (Bouhadir et al., *Ann. NY Acad. Sci.*, 842:188 (1998)). Cross-linking generally results in a relatively inert bioscaffold material which may induce a fibrous connective tissue response by the host to the scaffold material, inhibit scaffold degradation, and/or inhibit cellular infiltration into the scaffold. ECM scaffolds that are not cross-linked tend to be rapidly resorbed in contrast nonresorbable cross-linked materials or synthetic scaffolds such as Dacron or polytetrafluoroethylene (Bell, *Tissue Engin.*, 1:163 (1995); Bell, In: *Tissue Engineering: Current Perspectives*, Burhauser Pub. pp. 179-189 (1993); Badylak et al., *Tissue Engineering*, 4:379 (1998); Gleeson et al., *J. Urol.*, 148:1377 (1992)).

In accordance with the present invention, isolated ECM is used advantageously to decrease undesirable sequelae at the site of device implantation in a warm blooded vertebrate. A solid sheet, strip or loop of isolated ECM, or fluidized or powder forms of isolated ECM, may be applied to and/or fixed to a device. A sheet of isolated ECM is applied to (contacted with) or adhered to (fixed to) an implantable device. Particulate isolated ECM may be coated on an implantable device, and/or a gel form of ECM may be applied to an implantable device and subsequently lyophilized to form a coating. In one embodiment, ECM in sheet form is used to form coated implantable devices. Isolated ECM may be applied to or affixed to a device or to other isolated ECM materials, other bioscaffolds or other materials with anchoring projections (such as plastic or metal pins or sutures), adhesives, or other fixation devices known to those skilled in the art. In one embodiment, an isolated ECM sheet is sutured or otherwise secured to a device. For example, isolated ECM may be wrapped around the device and redundant tissue gathered and secured via sutures. Tissue segments or sheets are attached to each other before or during attachment to a device using surgically acceptable techniques, e.g., suturing, gluing, stapling or compressing. Multi-laminate constructs may be formed by overlapping individual strips of isolated ECM and applying pressure to the overlapped portions to fuse the strips together. In one embodiment, pressure is applied to the overlapped strips under conditions allowing dehydration of the isolated ECM.

Extracellular matrix embodiments include subject matter present in the following commonly assigned related applications which are incorporated by reference: "Lead Electrode Incorporation Extracellular Matrix," Ser. No. 11/017,238, filed Dec. 20, 2004; "Implantable Medical Devices Comprising Isolated Extracellular Matrix," Ser. No. 11/017,432, filed Dec. 20, 2004; "Use of Extracellular Matrix and Electrical Therapy," Ser. No. 11/017,237, filed Dec. 20, 2004; and "Epicardial Patch Including Isolated Extracellular Matrix with Pacing Electrodes," Ser. No. 11/017,627, filed Dec. 20, 2004.

One example of an embodiment with extracellular matrix includes extracellular matrix disposed around the exterior of the secondary body 1110. In various embodiments, the steerable extravascular lead body 1112 punctures the main lead body 1106. Following puncture, an assembly capable of puncturing tissue is advanced through the main body. In one example, the assembly includes a probe 1108, and a secondary body 1110. In various embodiments, the probe 1108 and secondary body 1110 puncture vasculature, and advance until extracellular matrix coating the secondary body is in contact with the tissue opening created by the puncture. In various embodiments, the probe is additionally advanced, placing an electrode in the IVC-LA fat pad. In one example, the probe 1108 includes an electrode capable of monitoring physiological data, and additionally capable of electrically stimulating neural cells located in the IVC-LA fat pad.

In various embodiments, the lead includes a portion with a different strength than other portions of the wall of the puncture body lumen 1104, creating an area of weakened resilient material 1114. The area of weakened resilient material 1114 can assist in an effort for the steerable extravascular lead body 1112 to break through the puncture body lumen 1104 of the main lead body 1106. In various embodiments, the area of weakened resilient material is a special portion of main lead body 1106 with less material than areas near the vicinity of the area of weakened resilient material. Additionally, the area of weakened resilient material is, in various embodiments, delineated with radioopaque markers. Various radioopaque markers are within the scope of the present subject matter, including fluoroscopic materials impregnated in the lead. Radioopaque markers, in various embodiments, assist one in finding the area of weakened resilient material 1114 during fluoroscopy.

Figure 12A:
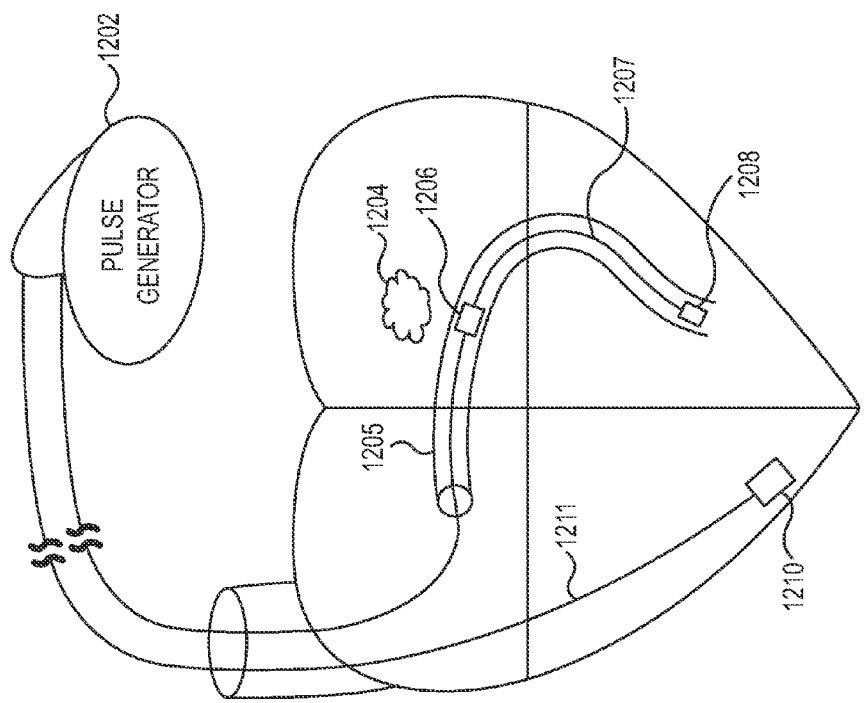
FIG. 12A shows a device adapted to deliver neural stimulation and cardiac resynchronization therapy, according to various embodiments of the present subject matter.

FIG. 12A shows a system diagram of a microprocessor-based cardiac device suitable for practicing the present subject matter. The device 1202 is equipped with multiple sensing and pacing channels which is configured to sense various myocardial events, and which can additionally pace multiple sites in the atria or the ventricles, or in both. For example, the device is configured for cardiac resynchronization pacing of the atria or ventricles in various embodiments of the present subject matter, and in additional embodiments, can include configurations for delivering neural stimulation intended to influence the automatic nervous system, and in particular, to induce a parasympathetic response. Additionally, the device is useful for myocardial stress reduction pacing. For example, in one embodiment, one or more cardiac sites are sensed and paced in a manner that pre-excites at least one region of the myocardium.

In one example, the system includes a first lead 1121 integrated with a first electrode 1210 adapted to stimulate the right ventricle. Additionally, the system includes a second lead 1207 integrated with a second electrode 1206 and a third electrode 1208, the second electrode 1206 adapted to transvascularly stimulate neural fibers in the IVC-LA fat pad 1204. In various embodiments, the second lead 1207 is disposed in a coronary sinus 1205. In some examples, the first electrode 1210 and the third electrode 1208 are used in conjunction to deliver cardiac resynchronization therapy.

Figure 12B:
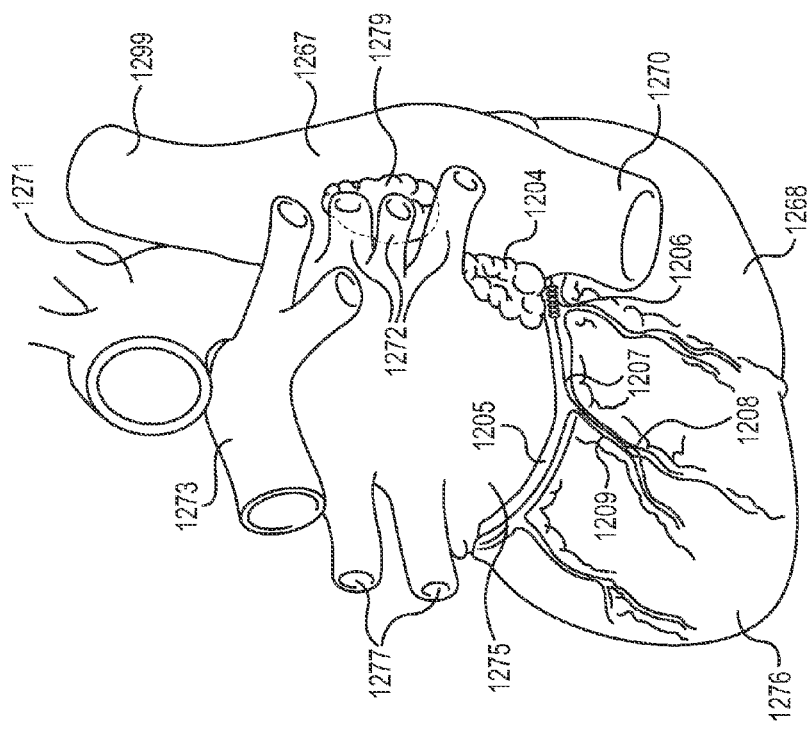
FIG. 12B shows a partially hidden view of a device adapted to deliver neural stimulation and cardiac resynchronization therapy, according to various embodiments of the present subject matter.

FIG. 12B illustrates the left atrium 1275, left ventricle 1276, right atrium 1267, right ventricle 1268, superior vena cava 1299, inferior vena cava 1270, aorta 1271, right pulmonary veins 1272, left pulmonary vein 1277, right pulmonary artery 1273, and coronary sinus 1205. FIG. 12B also illustrates a cardiac fat pad 1279 located proximal to the right cardiac veins and a cardiac fat pad 1204 located proximal to the inferior vena cava and left atrium.

The figures additionally illustrates an integrated lead 1207, including a third electrode 1208, and a second electrode 1206, as discussed in the teachings associated with FIG. 12A. In various embodiments, the lead is adapted for placement of the third electrode 1208 into a cardiac vein 1209.

Figure 13A:
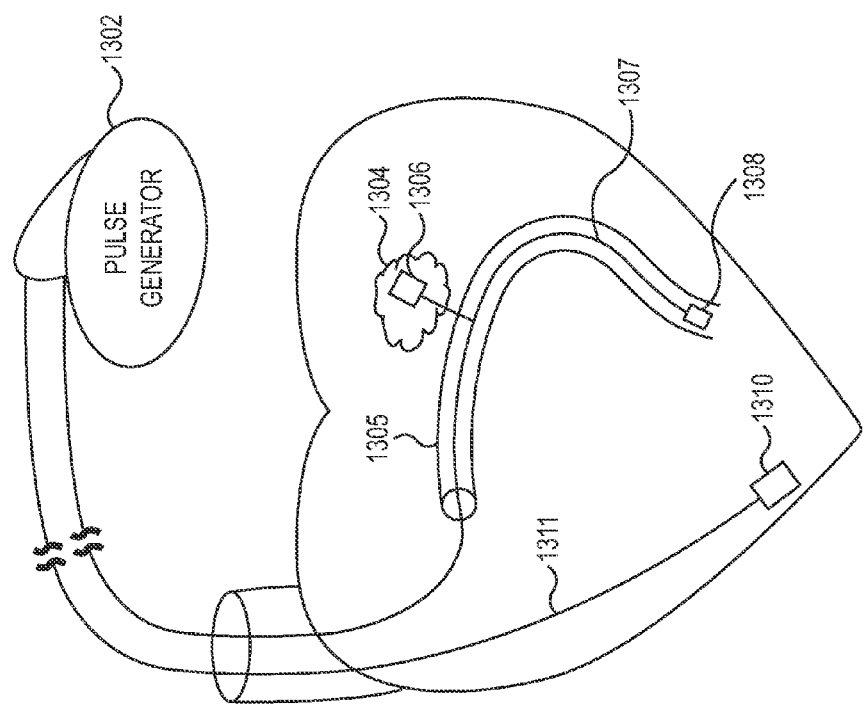
FIG. 13A shows a device adapted to puncture vasculature, according to various embodiments of the present subject matter.

FIG. 13A shows a system diagram of a microprocessor-based cardiac device suitable for practicing the present subject matter. The device 1302 is equipped with multiple sensing and pacing channels which is physically configured to sense various myocardial events, and which can additionally pace multiple sites in the atria or the ventricles, or in both. For example, the device is configured for cardiac resynchronization pacing of the atria or ventricles in various embodiments of the present subject matter, and in additional embodiments, can include configurations for delivering neural stimulation intended to influence the automatic nervous system, and in particular, to induce a parasympathetic response. Additionally, the device is useful for myocardial stress reduction pacing. For example, in one embodiment, one or more cardiac sites are sensed and paced in a manner that pre-excites at least one region of the myocardium.

In one example, the system includes a first lead 1131 integrated with a first electrode 1310 adapted to stimulate the right ventricle. Additionally, the system includes a second lead 1307 integrated with a second electrode 1306 and a third electrode 1308, the second electrode 1306 adapted to puncture vasculature and stimulate autonomic ganglia in the IVC-LA fat pad 1304. In various embodiments, the second lead 1307 is disposed in a coronary sinus 1305. In some examples, the first electrode 1310 and the third electrode 1308 are used in conjunction to deliver cardiac resynchronization therapy.

Figure 13B:
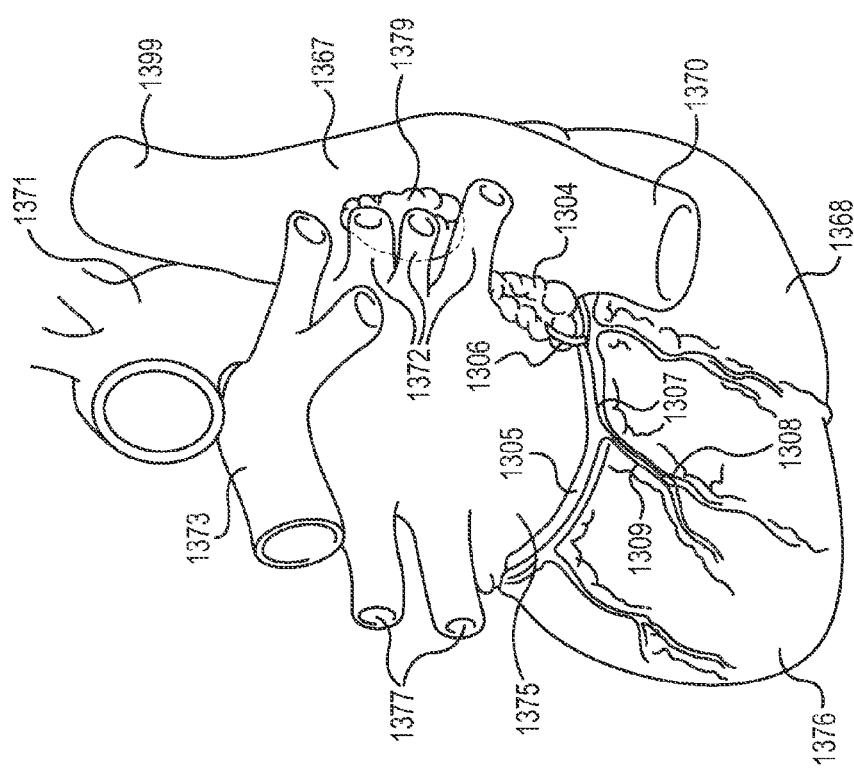
FIG. 13B shows a partially hidden view of a device to deliver neural stimulation and to puncture vasculature, according to various embodiments of the present subject matter.

FIG. 13B illustrates the left atrium 1375, left ventricle 1376, right atrium 1367, right ventricle 1368, superior vena cava 1399, inferior vena cava 1370, aorta 1371, right pulmonary veins 1372, left pulmonary vein 1377, right pulmonary artery 1373, and coronary sinus 1305. FIG. 13B also illustrates a cardiac fat pad 1379 located proximal to the right cardiac veins and a cardiac fat pad 1304 located proximal to the inferior vena cava and left atrium.

The figures additionally illustrates an integrated lead 1307, including a third electrode 1308, and a second electrode 1306, as discussed in the teachings associated with FIG. 13A. An additional teaching of the figure demonstrates the placement of the third electrode 1308 into a cardiac vein 1309.

Figure 14:
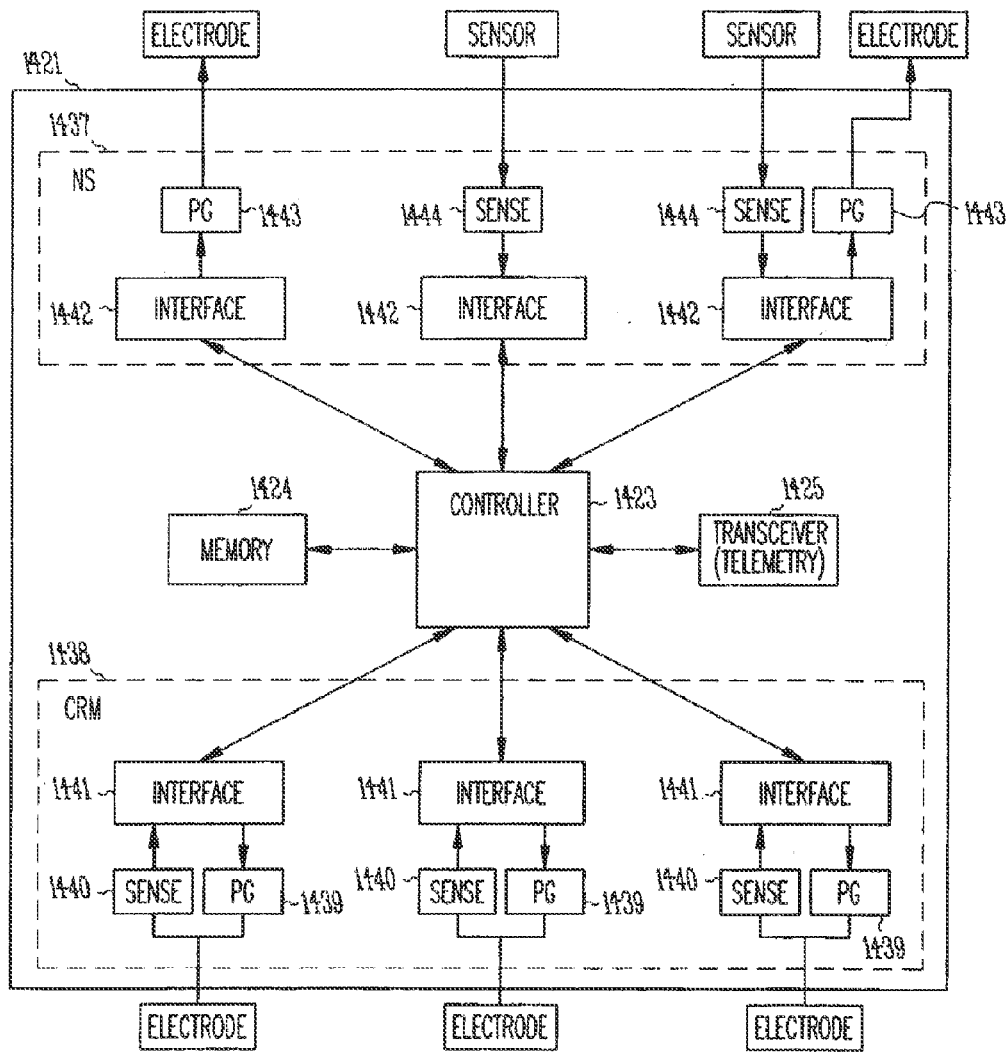
FIG. 14 illustrates a block diagram of an implantable medical device, according to one embodiments of the present subject matter.

FIG. 14 illustrates an implantable medical device 1421 such as that shown at 1202 in FIG. 12A having a neural stimulation component 1437 and cardiac rhythm management component 1438, according to various embodiments of the present subject matter. The illustrated device 1421 includes a controller 1423 and a memory 1424. According to various embodiments, the controller 1423 includes hardware, software, or a combination of hardware and software to perform fat pad stimulation and cardiac rhythm management functions. For example, the programmed therapy applications discussed in this disclosure are capable of being stored as computer-readable instructions embodied in memory and executed by a processor. According to various embodiments, the controller 1423 includes a processor to execute instructions embedded in memory to perform vagal nerve stimulation and cardiac rhythm management functions, including cardiac resynchronization therapy, and functions capable of promoting reductions in myocardial stress. The illustrated device 1421 further includes a transceiver 1425 and associated circuitry for use to communicate with a programmer or another external or internal device. Various embodiments include a telemetry coil.

The cardiac rhythm management therapy section 1438 includes components, under the control of the controller, to stimulate a heart and/or sense cardiac signals using one or more electrodes. The device is equipped with multiple sensing and pacing channels which is physically configured to sense and/or pace multiple sites in the atria or the ventricles. The multiple sensing/pacing channels are configured, for example, with one atrial and two ventricular sensing/stimulation channels for delivering biventricular resynchronization therapy and neural stimulation.

The cardiac rhythm management therapy section includes a pulse generator 1439 for use to provide an electrical signal through an electrode to stimulate a heart, and further includes sense circuitry 1440 to detect and process sensed cardiac signals. An interface 1441 is generally illustrated for use to communicate between the controller 1423 and the pulse generator 1439 and sense circuitry 1440. Three electrodes are illustrated as an example for use to provide cardiac rhythm management therapy. However, the present subject matter is not limited to a particular number of electrode sites. Each electrode can include its own pulse generator and sense circuitry. However, the present subject matter is not so limited. The pulse generating and sensing functions are multiplexed to function with multiple electrodes.

The neural stimulation ("NS") therapy section 1437 includes components, under the control of the controller, to stimulate a cardiac fat pad and/or sense automatic nervous system parameters associated with nerve activity or surrogates of automatic nervous system parameters such as blood pressure and respiration. Three interfaces 1442 are illustrated for use to provide automatic nervous system therapy. However, the present subject matter is not limited to a particular number interfaces, or to any particular stimulating or sensing functions. Pulse generators 1443 are used to provide electrical pulses to an electrode for use to stimulate a cardiac fat pad. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals.

Sense circuits 1444 are used to detect and process signals from a sensor, such as a sensor of nerve activity, blood pressure, respiration, and the like. The interfaces 1442 are generally illustrated for use to communicate between the controller 1423 and the pulse generator 1443 and sense circuitry 1444. Each interface, for example, is used to control a separate lead. Various embodiments of the neural stimulation therapy section only include a pulse generator to stimulate a cardiac fat pad. For example, the neural stimulation therapy section provides therapy promoting parasympathetic response.

One aspect of the present subject matter relates to a chronically-implanted stimulation system specially designed to minimize cardiac malfunction by stimulating parasympathetic ganglia to activate the autonomic reflex. Parasympathetic ganglia are located, for example, in a fat pad located proximal the inferior vena cava and the left atrium. In various embodiments, the system is integrated into a pacemaker/defibrillator or other electrical stimulator system. Components of the system include a high-frequency pulse generator, sensors to monitor blood pressure or other pertinent physiological parameters, leads to apply electrical stimulation to a cardiac fat pad, algorithms to determine the appropriate time to administer stimulation, and algorithms to manipulate data for display and patient management.

Various embodiments relate to a system that seeks to deliver electrically mediated neural stimulation therapy, such as therapy promoting parasympathetic response, to patients. Various embodiments combine a "stand-alone" pulse generator with a minimally invasive, unipolar lead that directly stimulates vagal nerves in the vicinity of the heart, such as in the IVC-LA fat pad. This embodiment is such that general medical practitioners lacking the skills of specialist can implant it. Various embodiments incorporate a simple implanted system that can sense parameters indicative of blood pressure. This system adjusts the therapeutic output (waveform amplitude, frequency, etc.) so as to maintain a desired quality of life. In various embodiments, an implanted system includes a pulse generating device and lead system, the stimulating electrode of which is positioned near endocardial vagal nerve tissues using transvenous implant technique(s).

Another embodiment includes a system that combines neural stimulation therapy with other therapies, such as cardiac resynchronization therapy. Some embodiments use an additional "fat pad lead" that emerges from the device header and is paced from a modified traditional pulse generating system.

Figure 15:
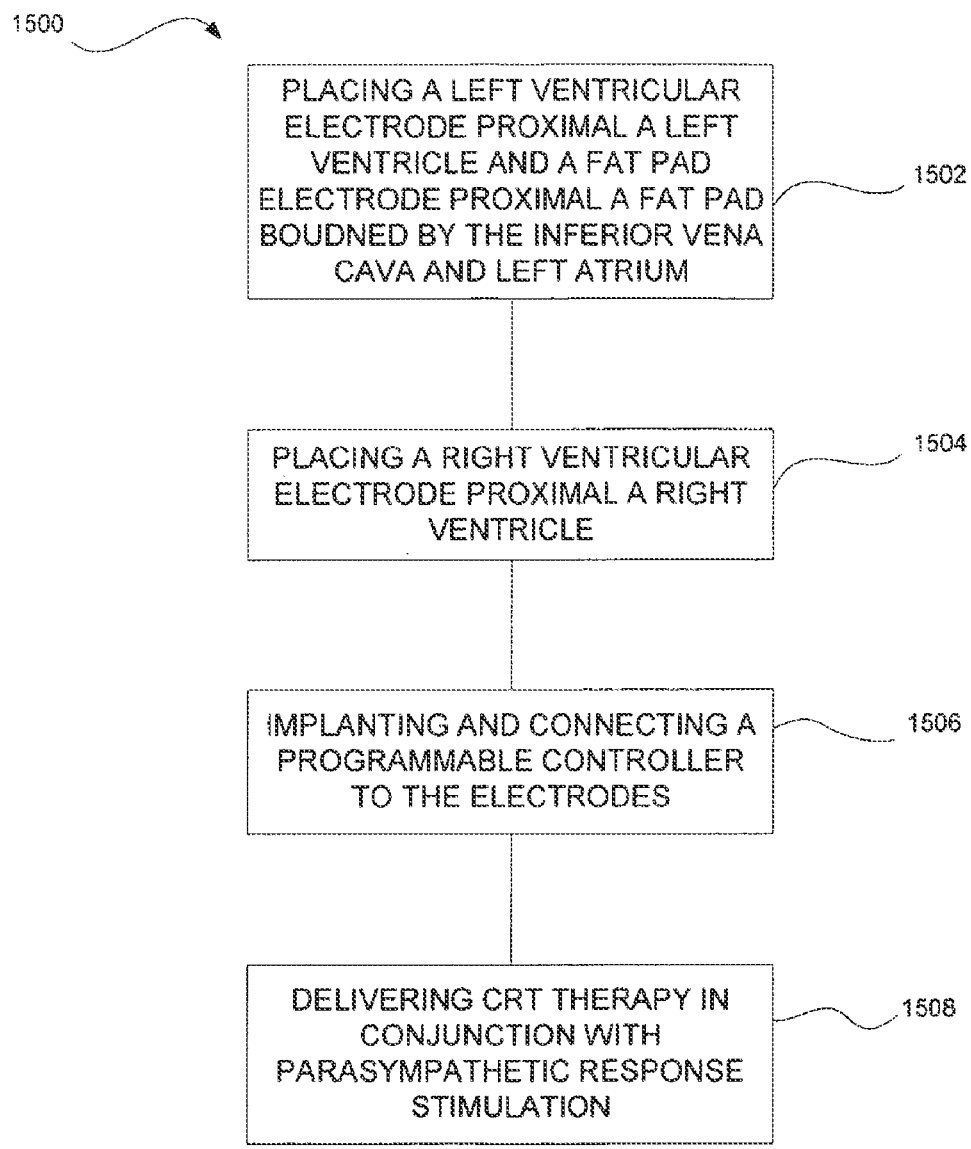
FIG. 15 shows a method for providing neural stimulation therapy and cardiac resynchronization therapy, according to one embodiment of the present subject matter.

FIG. 15 shows a method 1500 for providing neural stimulation therapy and cardiac resynchronization therapy, according to one embodiment of the present subject matter. In various embodiments, placing a left ventricular electrode proximal a left ventricle and a fat pad electrode proximal a fat pad bounded by the inferior vena cava and left atrium 1502. Additionally, some examples of the method include placing a right ventricular electrode proximal a right ventricle 1504. Also, various embodiments include implanting and connecting a programmable controller to the electrodes 1506. In additional embodiments, the method includes delivering cardiac resynchronization therapy in conjunction with parasympathetic response stimulation 1508.

Figure 16:
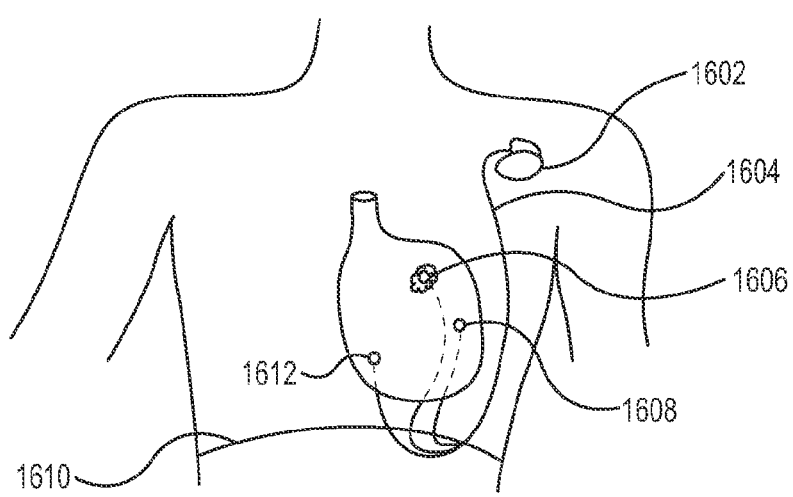
FIG. 16 shows a system with leads placed transxiphoidally, according to one embodiment of the present subject matter.

FIG. 16 shows a system diagram of a microprocessor-based cardiac device suitable for practicing the present subject matter, according to one embodiment of the present subject matter. A device 1602, connected by one or more leads 1604, interfaces with various aspects of patient anatomy to deliver parasympathetic response therapy through stimulation of parasympathetic ganglia in the IVC-LA fat pad simultaneous with delivering cardiac resynchronization therapy, using stimulation elements which are not placed in a traditional vascular manner, but which are inserted in a transxiphoidal process. For example, various embodiments place a first electrode 1612 proximal the right ventricle is implanted using a transxiphoidal process. Additional embodiments place a second electrode 1606 proximal the IVC-LA fat pad using a transxiphoidal process. One embodiment placed the second electrode 1606 partially within the IVC-LA fat pad transxiphoidal process. Also, various embodiments place a third electrode 1608 in a patient proximal the left ventricle using a transxiphoidal placement procedure.

In various embodiments, a transxiphoidal process places the electrodes in a patient by inserting them under the ribcage, and superior to the diaphragm 1610. In various embodiments, one or more electrodes are placed proximal target sites, and are either connected directly to myocardium, or are connected to epicedium, using various methods, including screw shaped electrodes, or electrodes which clasp portions of anatomy.

A transxiphoidal approach to the placement of the electrodes discussed in these teaching removes some size restrictions. For examples, a transxiphoidal lead can include one or more steering cables useful for directing a lead through tissue. Additionally, a transxiphoidal approach enables use of varied types of electrodes which normally could not be deployed through an intravenous approach.

Transthoracic approaches also can be used. For example, FIGS. 17A-17B illustrate various apparatus useful for deploying one or more electrodes in a transthoracic process, according to various embodiments of the present subject matter.

Figure 17A:
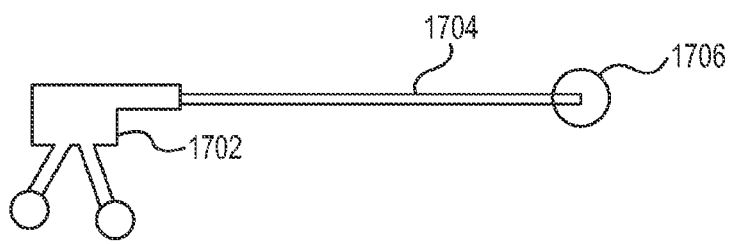
FIG. 17A illustrates an apparatus useful for deploying one or more electrodes in a transthoracic process, according to various embodiment of the present subject matter.

FIG. 17A illustrates a tool used for deploying one or more electrodes in a transthoracic process, according to one embodiment of the present subject matter. The tool, in various embodiments, includes a graspable portion 1702 adapted to provide leverage. In various embodiments, by holding the graspable portion 1702, one can insert an elongate rod 1704 into a patient in a transthoracic fashion. In various embodiments, the tool includes a tip 1706 adapted to manipulate and deploy an electrode.

Figure 17B:
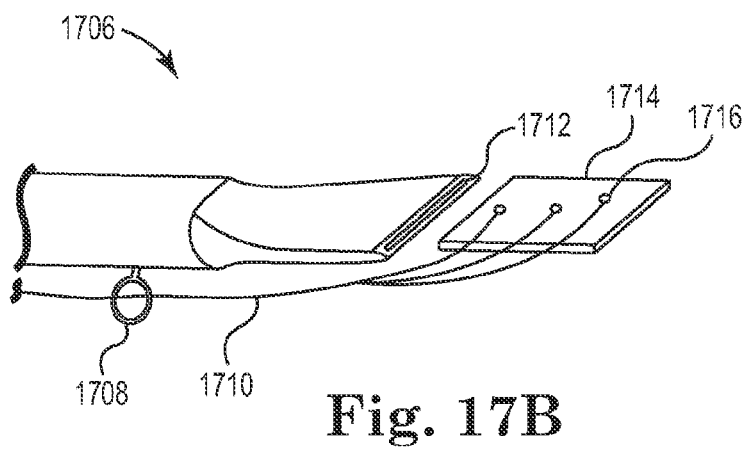
FIG. 17B illustrates an apparatus useful for deploying one or more electrodes in a transthoracic process, according to various embodiment of the present subject matter.

FIG. 17B illustrates on embodiment of a tip adapted to manipulate and deploy an electrode, according to one embodiment of the present subject matter. In various embodiments, the tip 1706 is adapted to carry one or more electrodes 1716, and deploy the one or more electrodes 1716 in a selective manner to various aspects of patient physiology. In various embodiments, the one or more electrodes 1716 are connected to a lead 1710 for connection to an implantable programmable pulse generator. For example, in one embodiment, one or more electrodes 1716 electrodes are deployed and fixed to the IVC-LA fat pad.

The tip 1706 and substrate 1714, in various embodiments, are adapted to position one or more electrodes 1716. In one embodiment, the tip 1706 is adapted to carry the substrate 1714 to control a mechanical bias. For example, in one embodiment, the tip 1706 includes an opening 1712 to which the substrate 1714 is mated. As the substrate 1714 is fed out of the opening 1712, the mechanical bias causes the substrate 1714 to curl, in various embodiments. As the substrate 1714 begins to curl, it affixes to patient physiology, such as the IVC-LA fat pad.

It should be noted that other electrode embodiments and electrode fixations are suitable for transthoracic deployment and are within the scope of the present subject matter.

In various embodiments, the substrate 1714 is a carrier for multiple electrodes. For example, one embodiment includes three electrodes. In this example, various electrodes 1716 are useful for adjusting device operation to improve efficiency of neural stimulation. For example, a combination of varied energy levels delivered to the electrodes 1716 improves neural capture and reduces energy requirements.

Additionally, in various embodiments, the tool is adapted to position an electrical lead 1710 in a patient. In one example, the tool includes carrying apparatus 1708 adapted for holding a lead and deploying the lead to a desired portion of patient anatomy.

Figure 17C:
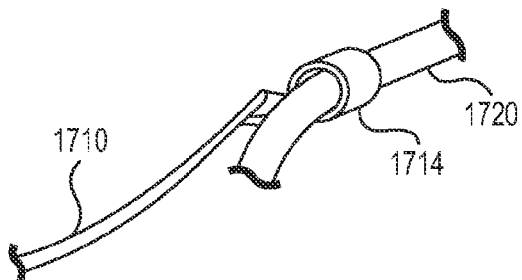
FIG. 17C illustrates an electrode placed proximal a vessel, according to one embodiment of the present subject matter.

FIG. 17C illustrates one example of a deployed lead 1710 and a deployed electrode substrate 1714. In various embodiments, an electrode substrate may grasp aspects of patient anatomy. One example grasps a vein 1720, however other aspects of patient physiology are compatible with the teachings of the present subject matter, and the present discussion should not be interpreted as exhaustive of exclusive.

A system according to these embodiments is used to augment partially successful treatment strategies. As an example, undesired side effects can limit the use of some pharmaceutical agents. The combination of a system according to these embodiments with reduced drug doses is particularly beneficial.

Figure 18:
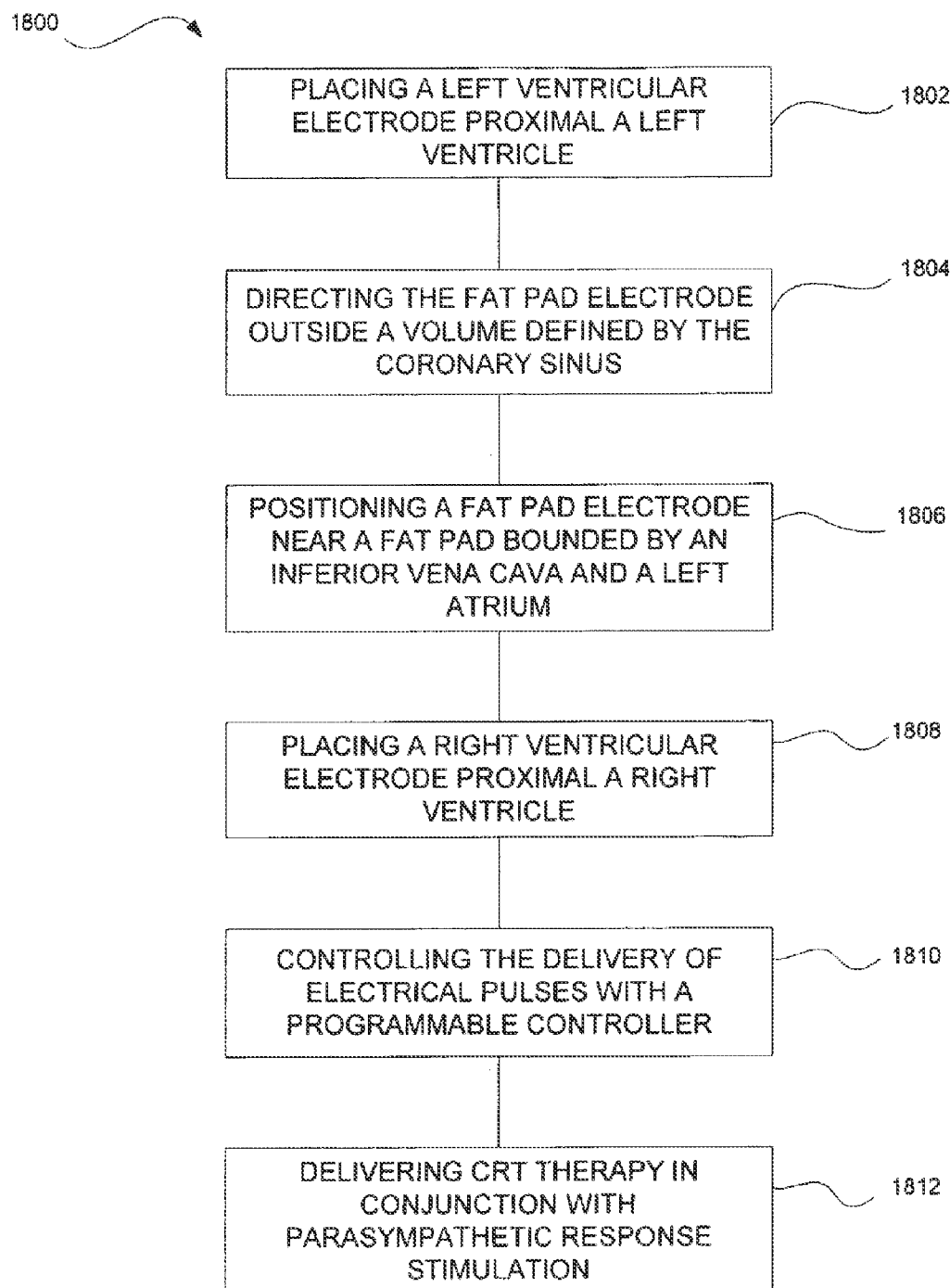
FIG. 18 illustrates a method for delivering cardiac resynchronization therapy in conjunction with parasympathetic response therapy for ventricular wall stress reduction, according to one embodiment of the present subject matter.

FIG. 18 shows a method 1800 for providing neural stimulation therapy and cardiac resynchronization therapy, according to one embodiment of the present subject matter. In various embodiments, the method includes placing a left ventricular electrode proximal a left ventricle 1802. Additionally the method includes directing the fat pad electrode outside a volume defined by the coronary sinus 1804. Also, the method includes positioning a fat pad electrode near a fad pad bounded by an inferior vena cava and a left atrium 1806. Additionally, some examples of the method include placing a right ventricular electrode proximal a right ventricle 1808. Also, various embodiments include controlling the delivery of electrical pulses with a programmable controller 1810. In additional embodiments, the method includes delivering cardiac resynchronization therapy in conjunction with parasympathetic response stimulation 1812.

Thus, according to various embodiments, the lead(s) and the electrode(s) on the leads are physically arranged with respect to the heart in a fashion that enables the electrodes to properly transmit pulses and sense signals from the heart, and with respect to vagal nerves to stimulate a parasympathetic response. As there is a number of leads and a number of electrodes per lead, the configuration is programmed to use a particular electrode or electrodes. According to various embodiments, the parasympathetic response is stimulated by stimulating autonomic ganglia located in the IVC-LA fat pads.

Programmed Therapy Applications

The present subject matter is suited to deliver one or both of selective neural stimulation and selective cardiac rhythm management functions. In some embodiments, the neural stimulation therapy provides therapy promoting parasympathetic response. These processes are performed by a processor executing computer-readable instructions embedded in memory, for example. These therapies include a number of applications, which have various processes and functions, some of which are identified and discussed in these teachings. The processes and functions of these therapies are not necessarily mutually exclusive, as some embodiments of the present subject matter include combinations of two or more of the identified processes and functions.

One of ordinary skill in the art will understand that the modules and other circuitry shown and described herein are implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods are within the scope of the present subject matter. The above-identified embodiments, and portions of the illustrated embodiments, are not necessarily mutually exclusive. These embodiments, or portions thereof, are combined in various embodiments. For example, various embodiments combine two or more of the illustrated processes. Two or more sensed parameters are combined into a composite parameter used to provide a desired neural stimulation, and in some embodiments, therapy which promotes parasympathetic response.

In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose can be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. An apparatus for delivering transvascular neural stimulation to a cardiac fat pad bounded by an inferior vena cava and a left atrium and myocardial stimulation to a left ventricle to reduce ventricular wall stress, the apparatus comprising:
   a main lead assembly having a proximal portion and a distal portion, the distal portion including a distal end of the main lead assembly, wherein the distal portion of the main lead assembly is adapted to be fed into a coronary sinus to place the distal end proximate to the left ventricle;
   a left ventricular electrode located on the distal end of the main lead assembly and adapted to be fed into the coronary sinus with the distal portion of the main lead assembly;
   a fat pad electrode adapted to be fed into the coronary sinus and disposed on the main lead assembly at a fixed distance from the distal end of the main lead assembly including the left ventricular electrode with both the left ventricular and fat pad electrodes being fixed on the main lead assembly, wherein the main lead assembly is sized such that the distance between the fat pad electrode and the distal end of the main lead assembly including the left ventricular electrode is such that the left ventricular electrode is configured to be located proximate to the left ventricle and the fat pad electrode is configured to be located in the coronary sinus at a position proximate parasympathetic ganglia located in the cardiac fat pad when the main lead assembly is implanted in the coronary sinus; and
   an implantable device connected to the proximal portion of the main lead, the device including a neural stimulation component adapted to use the fat pad electrode to deliver neural stimulation to stimulate the parasympathetic ganglia, a cardiac rhythm management component adapted to use the left ventricular electrode to deliver myocardial stimulation to the left ventricle, and a controller adapted to implement a programmed neural stimulation therapy to control the neural stimulation to the parasympathetic ganglia to reduce ventricular wall stress and to implement a programmed cardiac rhythm management therapy to control the myocardial stimulation to the left ventricle to reduce ventricular wall stress.

2. The apparatus of claim 1, wherein the main lead assembly includes a main lead body extending from the proximal portion of the main lead assembly and toward the distal end of the main lead assembly, the main lead body defining at least two lumens, one of the at least two lumens being adapted to receive a second lead body.

3. The apparatus of claim 1, wherein the main lead assembly includes a main lead body extending from the proximal portion of the main lead assembly and toward the distal end of the main lead assembly, the main lead body defining at least two lumens, one of the at least two lumens being adapted to receive a stylet.

4. The apparatus of claim 1, wherein the main lead assembly includes a main lead body extending from the proximal portion of the main lead assembly and toward the distal end of the main lead assembly, the main lead body defining at least two lumens, one of the at least two lumens being adapted to receive a guidewire.

5. The apparatus of claim 1, wherein the fat pad electrode includes at least one conductive band at least partially circumscribing the main lead body.

6. The apparatus of claim 5, wherein for each conductive band an insulated conductor is disposed in the main lead body and connected to the conductive band, the insulated conductor extending to the proximal portion of the main lead body.

7. The apparatus of claim 6, wherein the main lead assembly includes a vascular wall abutting helix shaped bias proximate the fat pad electrode.

8. The apparatus of claim 7, wherein the vascular wall abutting helix shaped bias includes predetermined bends in a wire coil in the main lead body.

9. The apparatus of claim 7, wherein the vascular wall abutting helix shaped bias includes predetermined bends in an insulator in the main lead body.

10. The apparatus of claim 1, wherein the implantable device is further connected to a second lead, the second lead sized for placement through a right atrium and in a right ventricle, the second lead adapted to deliver cardiac resynchronization therapy to reduce ventricular wall stress.

11. The apparatus of claim 1, further comprising one or more additional fat pad electrodes located on the main lead assembly at a fixed distance from the distal end of the main lead assembly including the left ventricular electrode.

12. A system for delivering neural stimulation to a cardiac fat pad bounded by an inferior vena cava and a left atrium and myocardial stimulation to a left ventricle to reduce ventricular wall stress, the system comprising:
   a lead assembly, including means sized for delivering a left ventricle electrode and a fat pad electrode into a coronary sinus and for positioning the left ventricle electrode proximate to the left ventricle and for positioning the fat pad electrode proximate to parasympathetic ganglia located in the cardiac fat pad, wherein a distance between the left ventricle electrode and the fat pad electrode is fixed on the lead assembly; and an implantable device to be connected to the lead assembly, the device including a neural stimulation circuit adapted to use the fat pad electrode to deliver neural stimulation to stimulate the parasympathetic ganglia, a cardiac rhythm management circuit adapted to use the left ventricular electrode to deliver myocardial stimulation to the left ventricle, and a controller circuit adapted to implement a programmed neural stimulation therapy to control the neural stimulation to the parasympathetic ganglia to reduce ventricular wall stress and to implement a programmed cardiac rhythm management therapy to control the myocardial stimulation to the left ventricle to reduce ventricular wall stress.

13. An apparatus for delivering neural stimulation to a cardiac fat pad bounded by an inferior vena cava and a left atrium and myocardial stimulation to a left ventricle to reduce ventricular wall stress, the apparatus comprising:

a main lead assembly having a proximal portion and a distal portion, the distal portion including a distal end of the main lead assembly, wherein the distal portion of the main lead assembly is adapted to be fed into a coronary sinus to place the distal end proximate to the left ventricle;

a left ventricular electrode located on the distal end of the main lead assembly and adapted to be fed into the coronary sinus with the distal portion of the main lead assembly;

a fat pad electrode adapted to be fed into the coronary sinus to advance the fat pad electrode to a position proximate parasympathetic ganglia located in the cardiac fat pad, wherein the fat pad electrode is disposed on the main lead assembly at a fixed distance from the distal end of the main lead assembly including the left ventricular electrode with both the left ventricular and fat pad electrodes being fixed on the main lead assembly, wherein the main lead assembly is sized such that the distance between the fat pad electrode and the distal end of the main lead assembly including the left ventricular electrode is such that the left ventricular electrode is configured to be located proximate to the left ventricle and the fat pad electrode is configured to be located at a position proximate parasympathetic ganglia located in the cardiac fat pad when the main lead assembly is implanted in the coronary sinus;

a second lead sized for placement through a right atrium and in a right ventricle, the second lead including a right ventricular electrode; and an implantable device connected to the second lead and to the proximal portion of the main lead, the device including a neural stimulation component adapted to use the fat pad electrode to deliver neural stimulation to stimulate the parasympathetic ganglia, a cardiac rhythm management component adapted to use the left ventricular electrode to deliver myocardial stimulation to the left ventricle and adapted to use the right ventricular electrode to deliver myocardial stimulation to the right ventricle, and a controller adapted to implement a programmed neural stimulation therapy to control the neural stimulation to the parasympathetic ganglia to reduce ventricular wall stress and to implement a programmed cardiac resynchronization therapy to control the myocardial stimulation to the right ventricle and the left ventricle to reduce ventricular wall stress.

14. The apparatus of claim 13, wherein the main lead assembly includes a main lead body extending from the proximal portion of the main lead assembly and toward the distal end of the main lead assembly, the main lead body defining at least two lumens, one of the at least two lumens being adapted to receive a second lead body.

15. The apparatus of claim 13, wherein the main lead assembly includes a main lead body extending from the proximal portion of the main lead assembly and toward the distal end of the main lead assembly, the main lead body defining at least two lumens, one of the at least two lumens being adapted to receive a stylet.

16. The apparatus of claim 13, wherein the main lead assembly includes a main lead body extending from the proximal portion of the main lead assembly and toward the distal end of the main lead assembly, the main lead body defining at least two lumens, one of the at least two lumens being adapted to receive a guidewire.

17. The apparatus of claim 13, further comprising one or more additional fat pad electrodes located on the main lead assembly at a fixed distance from the distal end of the main lead assembly including the left ventricular electrode.

18. An apparatus for delivering transvascular neural stimulation to a cardiac fat pad bounded by an inferior vena cava and a left atrium and myocardial stimulation to a left ventricle to reduce ventricular wall stress, the apparatus comprising:

a lead body having a proximal portion and a distal portion, the distal portion including a distal end of the lead body adapted to be fed into a coronary sinus to place the distal end of the lead body proximate to the left ventricle;

a left ventricular electrode located on the distal end of the lead body;

two or more fat pad electrodes disposed on a proximal portion of the lead body, each at a fixed distance from the distal end of the lead body including the left ventricular electrode with both the left ventricular and fat pad electrodes being fixed on the main lead body, wherein the lead body is sized such that the distance between at least one of the fat pad electrodes and the distal end of the lead body including the left ventricular electrode is such that the left ventricular electrode is configured to be located proximate to the left ventricle and at least one fat pad electrode is configured to be located in the coronary sinus at a position proximate parasympathetic ganglia located in the cardiac fat pad when the lead body is implanted in the coronary sinus; and an implantable device connected to the proximal portion of lead body, the implantable device including a neural stimulation component adapted to use the fat pad electrode to deliver neural stimulation to stimulate the parasympathetic ganglia, a cardiac rhythm management component adapted to use the left ventricular electrode to deliver myocardial stimulation to the left ventricle, and a controller adapted to implement a programmed neural stimulation therapy to control the neural stimulation to the parasympathetic ganglia to reduce ventricular wall stress and to implement a programmed cardiac rhythm management therapy to control the myocardial stimulation to the left ventricle to reduce ventricular wall stress.

19. The apparatus of claim 18, wherein the proximal portion of the lead body comprises a vascular wall abutting helix shaped bias.

20. The apparatus of claim 19, wherein the vascular wall abutting helix shaped bias includes predetermined bends in a wire coil in the proximal portion of the lead body.

21. The apparatus of claim 19, wherein the vascular wall abutting helix shaped bias includes predetermined bends in an insulator in the lead body.

22. The apparatus of claim 19, wherein the implantable device is further connected to a second lead, the second lead sized for placement through a right atrium and in a right ventricle, the second lead adapted to deliver cardiac resynchronization therapy to reduce ventricular wall stress.

23. The apparatus of claim 19, wherein the lead body comprises one or more lumens extending from a proximal portion towards a distal end of the lead body.

* * * * *